(12) United States Patent
Ozawa et al.

(10) Patent No.: US 6,327,493 B1
(45) Date of Patent: Dec. 4, 2001

(54) LIGHT SCANNING DEVICES OF A WATER-TIGHT STRUCTURE TO BE INSERTED INTO A BODY CAVITY TO OBTAIN OPTICAL INFORMATION ON INSIDE OF A BIOLOGICAL TISSUE

(75) Inventors: Takeshi Ozawa, Tama; Mamoru Kaneko, Hanno; Akihiro Horii, Hachioji; Atsushi Okawa, Hachioji; Hiroki Hibino, Hachioji; Hiroyuki Sangu, Hino; Hitoshi Ueno, Hachioji; Hitoshi Mizuno, Koganei; Jun Hiroya, Tokyo; Katsuichi Imaizumi, Hachioji; Hidemichi Aoki, Tokorozawa; Masahiro Ohno, Kunitachi; Eiji Yasuda, Hachioji; Yoshinao Oaki, Hino; Kenji Yoshino, Hachioji; Sakae Takehana, Sagamihara; Isami Hirao, Hino; Takefumi Uesugi; Toshimasa Kawai, both of Hachioji, all of (JP)

(73) Assignee: Olympus Optical Co., Ltd., Tokyo (JP)

( * ) Notice: Subject to any disclaimer, the term of this patent is extended or adjusted under 35 U.S.C. 154(b) by 0 days.

(21) Appl. No.: 09/141,572

(22) Filed: Aug. 27, 1998

(30) Foreign Application Priority Data

Aug. 28, 1997 (JP) .................................... 9-233001
May 28, 1998 (JP) .................................. 10-148046

(51) Int. Cl.[7] .................................................. A61B 6/00

(52) U.S. Cl. .......................... 600/476; 600/478; 602/1; 356/318; 356/345; 356/360; 348/45; 359/477

(58) Field of Search ................................ 600/310, 312, 600/342, 407, 425, 426, 473, 476, 478, 104, 105, 108, 109, 110, 111–189; 602/1; 356/318, 345, 360; 348/45; 359/477

(56) References Cited

U.S. PATENT DOCUMENTS

| 4,718,417 | * | 1/1988 | Kittrell et al. | 606/7 |
|---|---|---|---|---|
| 4,986,262 | * | 1/1991 | Saito et al. | 128/6 |
| 5,120,953 | | 6/1992 | Harris | 250/227.2 |
| 5,161,053 | | 11/1992 | Dabbs | 359/384 |
| 5,305,759 | * | 4/1994 | Kaneko et al. | 128/665 |
| 5,321,501 | | 6/1994 | Swanson et al. | 356/345 |
| 5,383,467 | | 1/1995 | Auer et al. | 128/664 |
| 5,434,669 | * | 7/1995 | Tabata et al. | 356/345 |

(List continued on next page.)

FOREIGN PATENT DOCUMENTS

| 6511312 | 12/1994 | (JP) . |
| 9-230248 | 9/1997 | (JP) . |
| 92/19930 | 11/1992 | (WO) . |

OTHER PUBLICATIONS

G.J. Tearney, et al., "In Vivo Endoscopic Optical Biopsy With Optical Coherence Tomography", Science, vol. 276, Jun. 27, 1997, pp. 2037–2039.

D.L. Dickensheets, et al., "Micromachined Scanning Confocal Optical Microscope", Optics Letters, vol. 21, No. 10, May 15, 1996, pp. 764–766.

*Primary Examiner*—Marvin M. Lateef
*Assistant Examiner*—Jeoyuh Lin
(74) *Attorney, Agent, or Firm*—Ostrolenk, Faber, Gerb & Soffen, LLP

(57) ABSTRACT

A light scanning device has a tip structure which includes a light scanning part connected to a light source, and which is insertable into a body cavity and is formed so as to be water-tight. A controlling part controls the light scan through the tip structure, and the tip structure and the controlling part are also connected to each other in a water-tight manner by a slender tube through which a plurality of electrical cables pass. An electric connector is fixed with the proximal end portion of the tube in a water-tight manner, and is electrically connectable so as to be water-tight with and removable from this controlling part.

48 Claims, 19 Drawing Sheets

U.S. PATENT DOCUMENTS

| | | | |
|---|---|---|---|
| 5,439,000 | 8/1995 | Gunderson et al. | 128/664 |
| 5,459,570 | 10/1995 | Swanson et al. | 356/345 |
| 5,582,171 * | 12/1996 | Chornenky et al. | 128/653.1 |
| 5,601,087 | 2/1997 | Gunderson et al. | 128/664 |
| 5,743,847 * | 4/1998 | Nakamura et al. | 600/166 |
| 5,865,727 * | 2/1999 | Sano et al. | 600/178 |

* cited by examiner

LIGHT SCANNING DEVICES OF A WATER-TIGHT STRUCTURE TO BE INSERTED INTO A BODY CAVITY TO OBTAIN OPTICAL INFORMATION ON INSIDE OF A BIOLOGICAL TISSUE

BACKGROUND OF THE INVENTION

1. Field of the Invention

The present invention relates to light scanning devices and specifically light scanning devices characterized by the structural part of the light scanning probe.

2. Description of the Related Art

When a diagnosis is performed on a vital tissue, an imaging device is commonly used to obtain optical information on the surface conditions of the tissue. Developments in modern medicine, however, have progressed beyond the topical imaging device to provide an optical CT device by which optical information on the inside of the tissue can be obtained as well.

By this optical CT device, information on the inside of organisms are detected and tomograms are obtained using picosecond pulses of laser light. However, a laser light source which generates an extra short pulse light in a picosecond pulse order is expensive and large in size. Furthermore, such a laser light source is difficult to handle.

More recently, a coherence OCT (optical coherence tomogram) to obtain tomograms of a subject using a low coherence light has been disclosed in, for example, Japanese Patent Application Publication No. 6-511312.

Moreover, it is known to use light scanning confocal microscopes as a tool to observe vital tissue and cells in the direction of an optical axis at a high resolution. In this case, however, the regular confocal microscopes used for this purpose are large in size so that for observations, a sample is cut out into small pieces to be mounted on the microscope.

In addition, microconfocal endoscopes, i.e., miniaturized confocal microscopes, which are introduced into the alimentary tract and the like of organisms for observation have been disclosed in, for example, Japanese Unexamined Patent Publication No. 9-230248.

In the above-mentioned coherence OCT and microconfocal endoscopes, however, since a part of the light scanning probe is a non-water-tight structure, there are some drawbacks such as that when such as that when they are soaked into a washing/antiseptic solution after use, the solution leaks into the inside of the light scanning probe and thereby causes malfunctions.

SUMMARY OF THE INVENTION

One object of the present invention to provide a light scanning device which is able to solve the disadvantages caused by water leakage into the device.

Another object of the present invention is to provide a light scanning device which is able to prevent water leakage into the device through a connector which is a connection part between a light scanning probe and a controlling device.

A light scanning device of the present invention has a light scanning probe which possesses a light scanner to scan a light at the tip of the insertion part which can be inserted into a body cavity and which emits the light onto a subject area within the body cavity, and a controlling device in which said light scanning probe is installed in a removable way and which receives a detection signal and/or detection light of said light scanning probe, said light scanning probe including a probe main body having an insertion area and where said light scanner is made to be water-tight, and a connector which is fixed to said probe main body in a water-tight manner and which is connectable to said controlling device, thus avoiding any inconveniences due to water leakage into the light scanning device.

Other objects and advantages of the present invention will be sufficiently obvious by means of the following descriptions.

BRIEF DESCRIPTION OF THE DRAWINGS

FIG. 1 is a block diagram to show the structure of the light scanning probe.

FIG. 2 is a cross sectional view to show the structure of the electric connector to FIG. 1.

FIG. 3 is a block diagram to show the structure of the tip structure part of FIG. 1.

FIG. 4 is a block diagram to show the structure of an exemplary modification of the tip structure part of FIG. 3.

FIG. 5 is a block diagram to show the structure of the optical unit of FIG. 3.

FIG. 6 is a first illustrative diagram of FIG. 1 to illustrate a manufacturing method of the scan mirror of the optical unit of FIG. 5.

FIG. 7 is a second illustrative diagram of FIG. 2 to illustrate a manufacturing method of the scan mirror of the optical unit of FIG. 5.

FIG. 8 is a block diagram to show the structure of the controlling part of FIG. 1.

FIG. 9 is an illustrative diagram to illustrate the focal scanning by the optical unit of FIG. 5.

FIG. 10 is a cross sectional view to show the structure of an exemplary modification of the electric connector of FIG. 1.

FIG. 11 is a block diagram to show the structure of the light scanning device.

FIG. 12 is a block diagram to show the structure of the tip part of FIG. 11.

FIG. 13 is a cross sectional view to show the cross-section of the tip part of FIG. 11.

FIG. 14 is a cross sectional view to show the structure of the electric/light connector of FIG. 11.

FIG. 15 is a cross sectional view to show the structure of an exemplary modification of the electric/light connector of FIG. 11.

FIG. 16 is an elevational view to show the appearance of the light scanning probe.

FIG. 17 is a cross sectional view to show the detailed structure of the light scanning probe of FIG. 16.

FIG. 18 is a cross section to show an exemplary modification of the light scanning probe of FIG. 16.

FIG. 19 is a block diagram to show the structure of the light tomographic image device (light imaging device).

FIG. 20 is a schematic diagram to show an endoscope where the light scanning probe of FIG. 19 is inserted.

FIG. 21 is a cross sectional view to show the side part of the back end of the light scanning probe of FIG. 19.

FIG. 22 is a cross sectional view to show the over-all structure of the light scanning probe of FIG. 19.

FIG. 23 is a cross sectional view to show the structure of a first exemplary modification of the light scanning probe of FIG. 22.

FIG. 24 is a cross sectional view to show the structure of a second exemplary modification of the light scanning probe of FIG. 22.

FIG. 25 is an illustrative diagram to illustrate a water-tight cap to be installed onto the light scanning probe of FIG. 19.

FIG. 26 is a cross sectional view to show the side part of the front end of the light scanning probe of FIG. 19.

DESCRIPTION OF THE PREFERRED EMBODIMENTS

First Embodiment (Construction)

Figure 1:
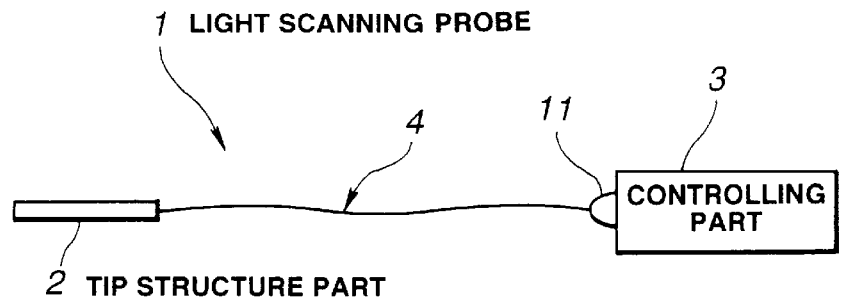
FIG. 1 to FIG. 10 relate to a first embodiment of the present invention.

As shown in FIG. 1, the light scanning probe 1 as the light scanning device of the embodiment of the present invention is composed of the tip structure part 2 which acts as the light scanning part possessing a light source and which can be inserted into a body cavity, and the controlling part 3 which controls the light scan by the tip structure part 2, wherein the tip structure part 2 and the controlling part 3 are connected to each other by a slender tube 4 in which plural electric cables pass through.

At the end part of the tube 4, an electric connector 11 is fixed thereto in a water-tight manner. Additionally, electric connector 11 is removably attached to controlling part 3 so as to provide an electrical connection therebetween.

Figure 2:
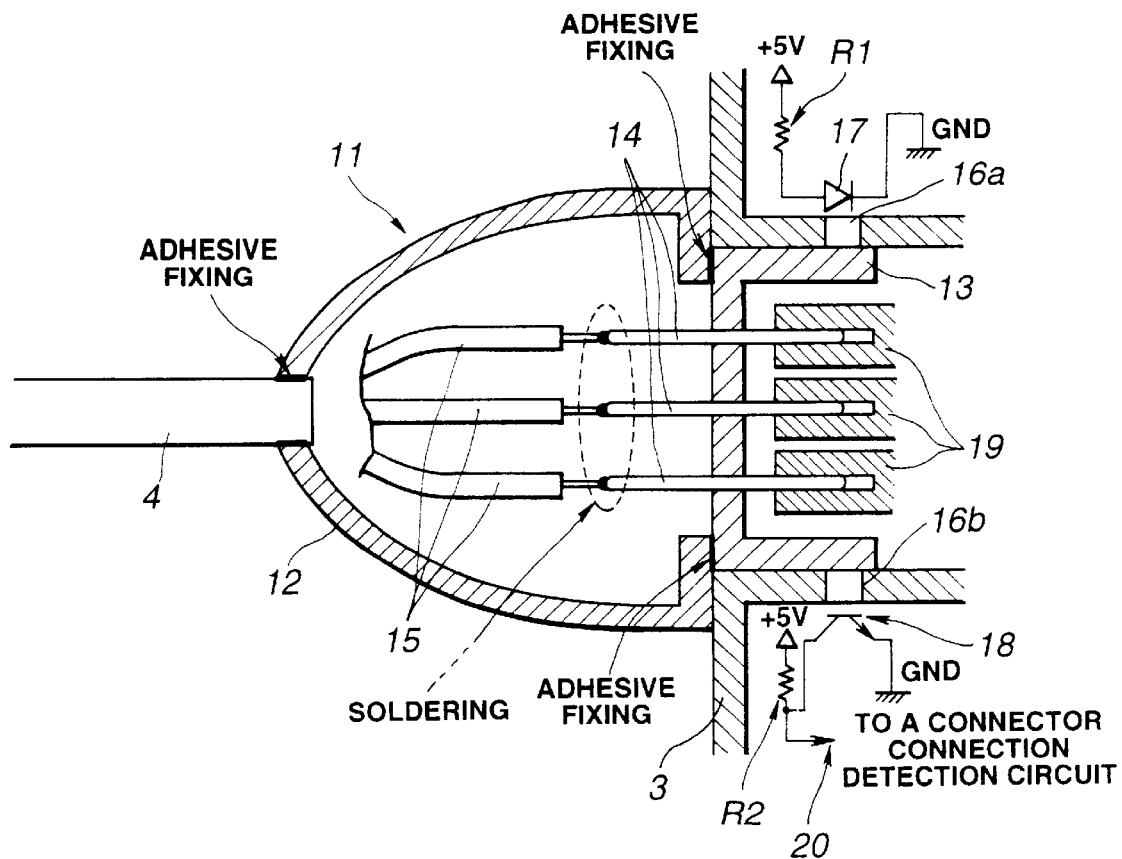

The cross section of the electric connector 11 is shown in FIG. 2. At the main body 12 of the electric connector 11, the connection part 13 is adhesively fixed in a water-tight manner as shown in FIG. 2. When the electric connector 11 is connected to the controlling part 3, the electric cables 15 which pass through the inside of the tube 4 are to be electrically connected to the electric cable 43, shown in FIG. 3 which will be described hereinafter, to control the optical unit 22 of FIG. 3. Conductive pins 14 and the electric cables 15 which pass through the inside of the tube 4 are soldered together as shown in FIG. 2. When the electric connector 11 is connected to the controlling part 3, the pins 14 contact and thereby become electrically connected to conductive pins 19 which are provided at the controlling part 3. In the controlling part 3, a photodiode 17 and a phototransistor 18 are provided adjacent locations therein which contact electric connector 11 when the electric connector 11 is connected to the controlling part 3. The photodiode 17 and the phototransistor 18 are each electrically connected to a resistor, a power source of +5V and a GND of 0 V to form individual electric circuits, respectively. Moreover, the phototransistor 18 is provided with an output part 20 to output operational signals. To realize its function, a hole 16a to let the outgoing light from the photodiode 17 pass through and a hole 16b to let the phototransistor 18 receive the outgoing light are respectively provided in controlling part 3.

The electric connector 11 is assembled as described herein. In short, the tube 4 and the electric connector 11 are first adhesively affixed to each other, and then the electric cables 15 and the connection part 13 are adhesively affixed to each other.

Figure 3:
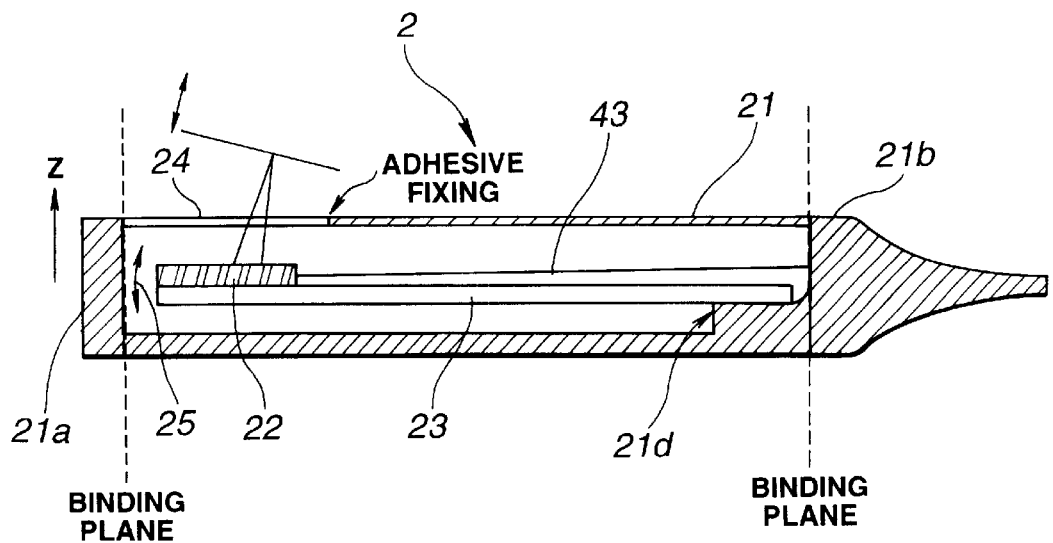

As shown in FIG. 3, the tip structure part 2 is composed of the main body 21, an optical unit 22 and a Z-axis actuator 23 which is movable in the direction of the Z axis as shown in the figure. Additionally, the main body 21 possesses a clear window part 24. The Z-axis actuator 23 is formed with a bimoroph piezoelectric actuator so that the optical unit 22 is actuated in the directions illustrated by arrows 25 by applying a voltage. One end of the Z-axis actuator 23 is bound to the main body 21, and the wiring from this Z-axis actuator 23 passes through the electric cable 43 and then is connected to the controlling part 3 which is shown in FIG. 1.

Here, the main body is a hollow pipe 21 having the optical unit 22 or the like in its interior, and a front cover 21a which closes the pipe 21 at its front end and a rear cover 21b which closes the pipe 21 from its base end are adhesively affixed to the pipe 21. Clear window part 24 is also adhesively fixed to pipe 21 so that the inside of the main body forms a water-tight structure.

The tip structure part 2 is assembled as described below. In short, the electric cable 43 is inserted in advance into the tube adhesively affixed to the rear cover 21b, and then the optical unit 22 and the Z-axis actuator 23 are bound to the hollow pipe 21 with which the window part 24 is adhesively fixed in advance. In other words, the optical unit 22 and the Z-axis actuator 23 are inserted in advance into the hollow pipe 21 while avoiding contact thereof with the inside of the pipe 21, and then the back end part of the Z-axis actuator is connected to the connection part 21d provided at the back end of the inside of the pipe 21. In this manner, light from the optical unit 22 is positioned so that it passes through the window part 24. Then, the rear cover 21b and the hollow pipe 21 are adhesively affixed together, and finally the front cover 21a is adhesively affixed to the pipe 21 as shown on the left side of FIG. 3.

Since the window part 24 and the connection part 21d are integrated into the pipe 21 when only the back end of the Z-axis actuator 23 to which the optical unit 22 is affixed in advance is adhesively fixed to this connection part 21d, the optical unit 22 is properly positioned at the position opposed to the window part 24. In this manner, assembly of the tip structure part 2 is designed to be relatively easy.

Figure 4:
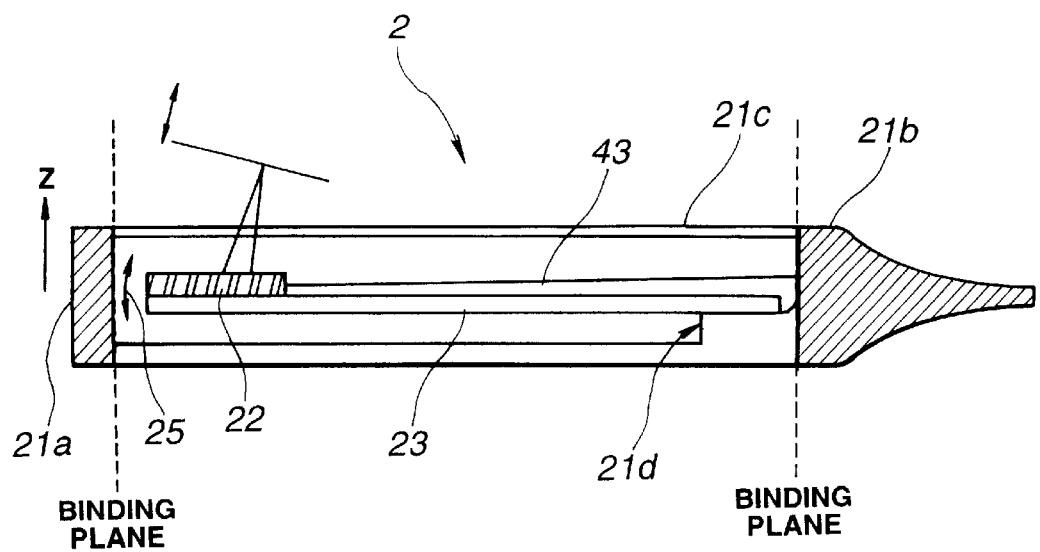

As an alternative, however, instead of the pipe 21 shown in FIG. 3, a clear hollow pipe 21c may be used and fixed so that the inside of the pipe 21c forms a water-tight structure as shown in FIG. 4. By using a clear pipe, assembly of the tip structure becomes even easier because the optical unit 22 is always assembled so as to be opposed to a clear part regardless of which direction optical unit 22 faces when being affixed during the assembly.

Figure 5:
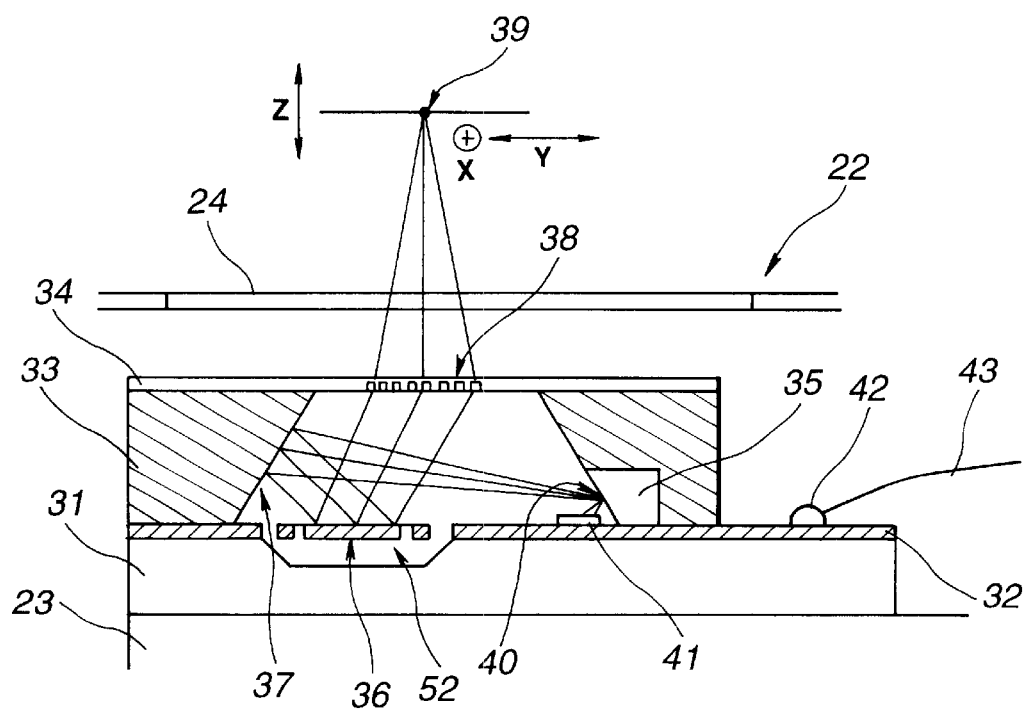

As shown in FIG. 5, the optical unit 22 includes a silicon substrate 31 which is bound with the end part of the Z-axis actuator 23, a plate 32 which is bound with said silicon substrate 31, a spacer 33 which is bound with said plate 32, and a top plate 34 which is bound with the spacer 33. To this spacer 33, a small semiconductor laser 35 which generates a laser beam having a wave length of 780 nm is adhesively fixed. Moreover, a scan mirror 36 is formed with the silicon substrate 31 and the plate 32, the scan mirror 36 being a constructed and mounted as a gimbal mirror. In addition, the spacer 33 includes a mirror part 37, and in the top plate 34, there is provided a diffraction grating lens 38.

Here, the optical unit elements are individually structured and positioned so that the light emitted from the semiconductor laser 35 is first reflected off of mirror part 37 of the spacer 33, then reflected off of scan mirror 36, and is finally passed through the diffraction grating lens 38 to focus on focal point 39.

In addition, a half mirror film 40 is provided at the outgoing end part of the semiconductor laser 35 but only at the area where the laser is emitted so as to cause a part of the returning light from the focal point 39 to be introduced onto the plane of the plate 32. Moreover, a photodiode 41 which detects light is provided on the plane of the plate 32 where the laser is introduced.

The scan mirror 36, the semiconductor laser 35 and the photodiode 41 are electrically connected to a land part 42 (contact point) through a pattern (not shown in the figure) on the plate 32, and the electric cable 43 is connected to the land part 42. Cable 43 then passes through the inside of the tube 4 and is connected to the controlling part 3 (see FIG. 1).

Next, the manufacturing process of the optical unit 22 will be explained.

A silicon substrate 31 with a low resistance value (about 10 Ωcm or less) is used, and on its upper surface in all areas other than that where dent 52 is to be formed, a mask is applied by, for example, a resist or the like. Then, dent 52 is formed by, for example, an anisotropy wet etching method or a dry etching method using KOH, TMAH or the like. The depth of the dent 52 is determined so as to be sufficient to cover the movable range of the scan mirror 36.

The plate 32 is made of silicon, and is joined with the silicon substrate 31 by forming an oxide layer (not shown) of $SiO_2$ or the like on the surface of the silicon substrate 31 between the joinings. Here, the plate 32 and the silicon substrate 31 are electrically insulated by an insulating film layer which is not shown in the figure.

Then after the plate 32 is joined with the silicon substrate 31, the scan mirror 36 and the other elements are added by appropriate processes. Specifically, on the surface of the plate 32, a nitride film is deposited by the CVD (Chemical Vapor Deposition) method or the like, and is then processed by a photolithography method/etching method to produce the scan mirror 36.

Figure 6:
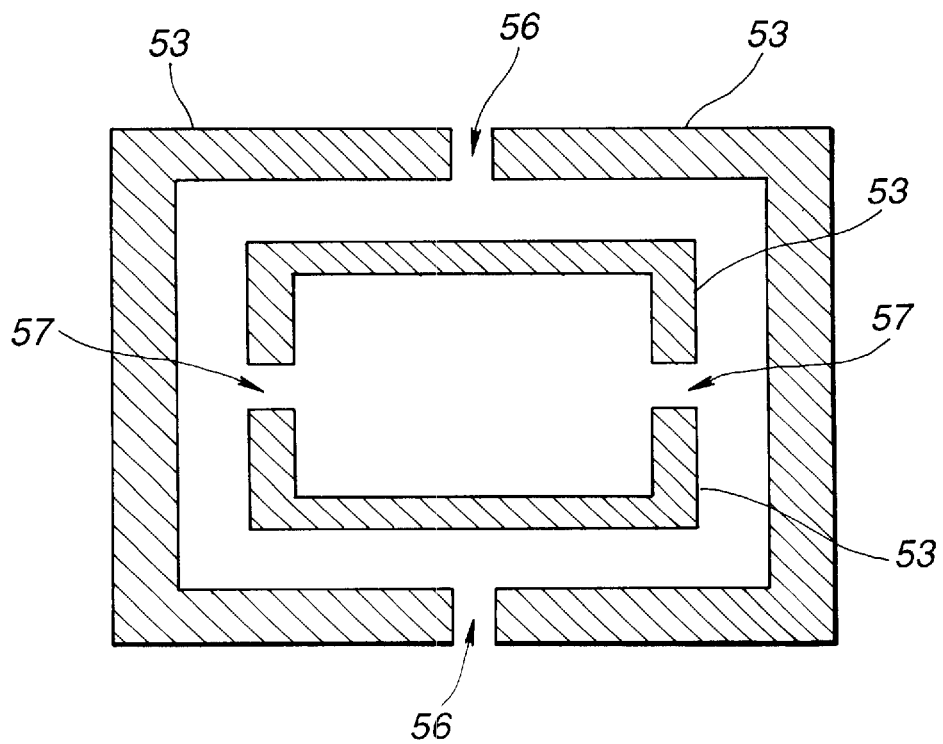

A plan view is shown in FIG. 6 in which the scan mirror is viewed from the top. The shaded portions 53 represent the areas where nitride film mask was not applied prior to processing the plate 32 by the etching method. The white areas represent the areas which were covered with the nitride film.

Figure 7:
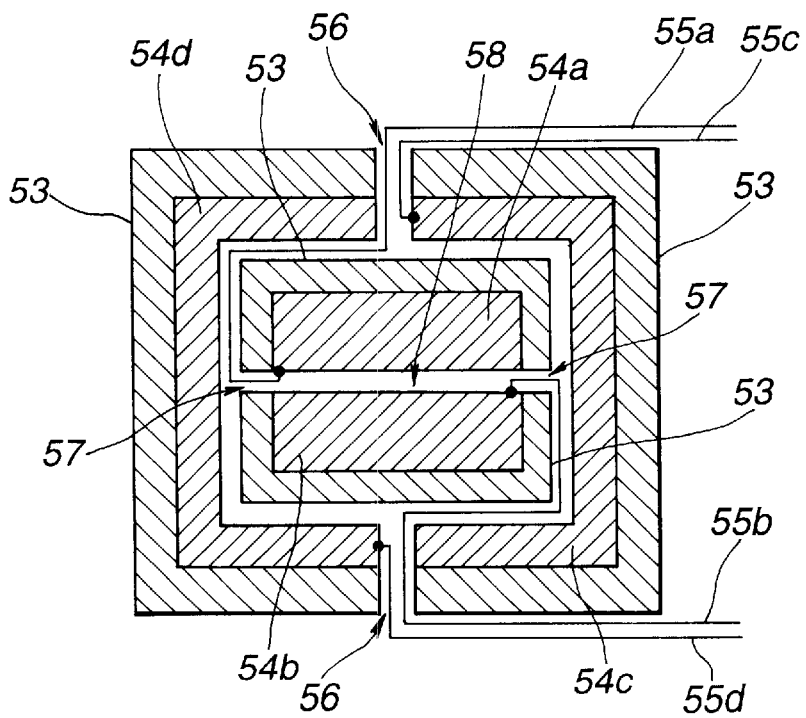

Before etching the plate 32, a conductive film layer is selectively formed thereon by depositing a metal thin film such as aluminum or the like and then forming a pattern by the photolithography method. The conductive film layer includes electrodes 54a, 54b, 54c, 54d and wires 55a, 55b, 55c, 55d, and the like of the scan mirror 36 as shown in FIG. 7. The patterns of these wires 55a, 55b, 55c, and 55d are connected toward the land part 42, whereupon the wire of the semiconductor laser 35 (not shown), the wire of the photodiode 41 (not shown) and the land part 42 merge to form electric cable 43. Here, the electrodes 54a, 54b, 54c and 54d also concurrently function as mirrors.

After the formation and photolithographic processing of the conductive layer, a silicon nitride film is applied as a mask to produce the scan mirror 36 and the like by etching the plate 32. However, when the electrodes 54a–54d are eroded by an etching solution or an etching gas, the surface of these conductive patterns can be protected using resists or the like.

By this etching process, the portions of the plate 32 which correspond to the shaded portions 53, which are not covered by the nitride film as shown in FIG. 6, is etched away to form the scan mirror 36 with a gimbal structure or the like. To produce the hinge parts 56 and 57 of the scan mirror 36, the nitride film mask is left on those areas to result in underetching from both sides thereof, thus enabling the center part 58 of the scan mirror 36 to become two-dimensionally rotatable in the X direction and Y direction upon the hinge parts 56 and 57 as the axes.

The photodiode 41, which is separately manufactured, is affixed to plate 32 and is in electrical contact with wires on the plate 32. Although in the exemplary embodiment of the present invention discussed herein, the photodiode 41 is manufactured separately and affixed to plate 32, the photodiode alternatively may be manufactured directly onto the plate 32 or the silicon substrate 31 with the above-mentioned semiconductor process.

Referring back to FIG. 5, the spacer 33 is made of silicon and an opening is made by etching the silicon with a photolithography method and an etching method. In particular, the opening is shaped so that the mirror part 37 can be formed on the inner surface of one side thereof, and so that the separately manufactured semiconductor laser 35 can be guided and fixed on another surface thereof. The mirrored surface of the mirror part 37 is formed by sputtering or vapor deposition after processing the silicon surface as detailed above. When the mirror part 37 is made of aluminum, the most suitable thickness is 150–200 nm.

This spacer 33 is affixed to the plate 32 to provide electrical contact between the wire provided at the bottom face of the semiconductor laser 35 and the wire provided at the plate 32.

Although the embodiment of the present invention as described herein, the semiconductor laser 35 is separately manufactured and integrated into the spacer 33, the semiconductor laser 35 alternatively may be directly manufactured onto the spacer 33 at the time of manufacturing the spacer 33.

The top plate 34 is made of quartz glass and is affixed to the spacer 33. Additionally, top plate 34 includes the diffraction grating lens 38 which is manufactured by transferring the pattern by electron light lithography and anisotropy reactive ion etching.

Figure 8:
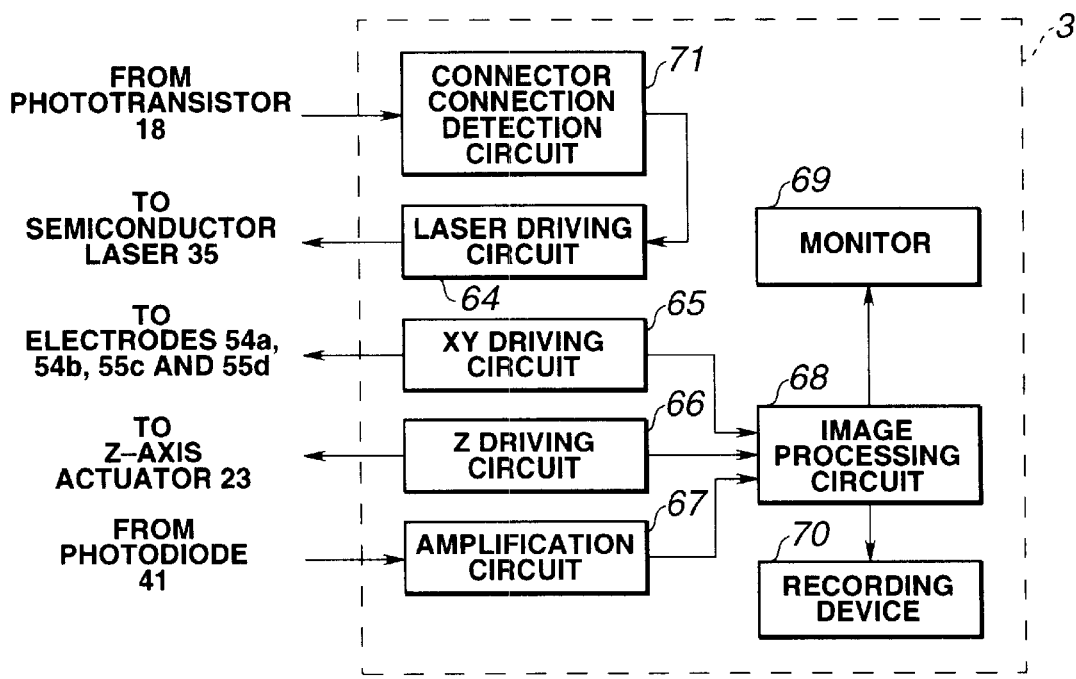

As shown in FIG. 8, the controlling part 3 includes a laser driving circuit 64 which drives and controls the semiconductor laser 35, a XY driving circuit 65 which is connected to the electrodes 54a, 54b, 54c, and 54d to drive the scan mirror 36 and conducts XY scan, a Z driving circuit 66 which drives the Z-axis actuator 23 and conducts Z scan, an amplifying circuit 67 which amplifies the detection signals from the photodiode 41, a connector connection detection circuit 71 which detects the connection conditions of the electric connector 11 using signals from the phototransistor 18 and controls the laser driving circuit 64 so that the electric connector 11 can emit laser light when it is connected, an image processing circuit 68 which receives the driving signals from the XY driving circuit 65 and the Z-axis driving circuit 66 and generates scanning images based on the detection signals which the amplifying circuit 67 amplifies, a monitor 69 which displays the scanning images which the image processing circuit 68 generates, and a recording device 70 which records the scanning images which the image processing circuit 68 generates.

(Operation)

The laser light is emitted from the semiconductor laser 35 which is driven by the laser driving circuit 64. This laser light is reflected off the mirror part 37 as shown in FIG. 5, then is reflected off the scan mirror 36, and finally passed through the diffraction grating lens 38 of the top panel to focus at focal point 39. When an object is placed at the position of the focus 39 and the emitted light is reflected therefrom, the reflected light passes through the same optical path as that of the incident light, and then is focused again at the exit hole (not shown) of the semiconductor laser 35, whereby a part of the light is introduced into the photodiode 41 by the half mirror film 40 provided at the end part of semiconductor laser 35.

In this process, the reflected light beams from the focus point return through the same optical paths as that of the incident light beams and refocus on the end plane of the exit hole of the semiconductor laser 35. Since the half mirror film 40 is provided only at the laser exit hole, most of the returning light does not focus there and therefore is only partially reflected by the half mirror film 40 so that only a portion of the reflected light enters the photodiode 41. In other words, the half mirror film 40 of this semiconductor laser 35 serves as a small pin hole to form a confocal optical system.

Under such conditions, when the electrodes 54a and 54b of the scan mirror are alternately charged by the XY driving circuit 65 of the controlling part 3 and the silicon substrate 31 is connected to the ground, the electrodes 54a and 54b of the scan mirror, when each of them is positively charged, pulls against the substrate with the power of static electricity causes the center part 58 of the scan mirror 36 to pivot around the hinge 57 as the rotation axis. Correspondingly, the position of the focus 38 of the laser light is scanned in the X direction of the scanning plane (in the vertical direction against the plane of the sheet) as shown in FIG. 5. Similarly, by alternately charging the electrodes 54c and 54d positively, the center part 58 of the scan mirror 36 rocks around the hinge 56 as the rotation axis. As a result, the position of the focus 39 of the laser light is scanned in the Y direction of the scanning plane (orthogonal to the X direction).

Figure 9:
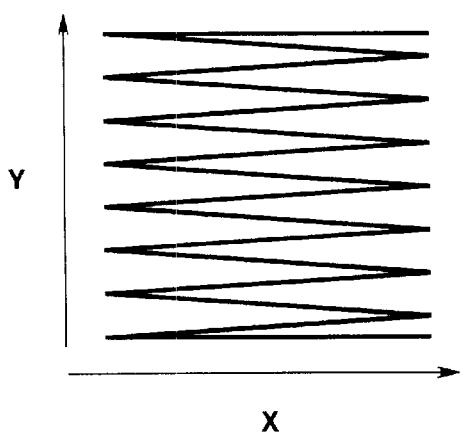

Here, by making the oscillation frequency in the Y direction sufficiently slow compared to the frequency of the scanning in the X direction, by controlling the scanning according to an appropriate timing, the focus 39 scans the plane of the subject in sequence as shown in FIG. 9. By this process, reflected light from every point of the plane of the scanned subject is received at the photodiode 41.

The light beams are converted to electric signals by the photodiode 41, and these electric signals are amplified at the amplifying circuit 67 of the controlling part 3. The signals which are amplified there are transferred to the image processing circuit 68. At the image processing circuit 68, the signals are computed to identify which focus position each signal originates from by referring to the driving waveforms of the XY circuit 65. Further, the intensities of the reflected lights at the individual points are computed in image processing circuit 68 to be displayed accordingly on the monitor. By repeating this process, the reflected lights from the scanning plane are imaged on the monitor. In addition, the image date can be recorded onto the recording device 70 as needed.

Moreover, by driving the Z-axis actuator 35 with the Z driving circuit 66, it is possible to shift the focus position in the Z direction as shown in FIG. 4. By incorporating the images obtained in the manner described above, images of the viewed sample which can be shifted in the Z direction of the sample can be observed. Furthermore, the image processing circuit 68 records the data of a plurality of scanned images from different positions in the Z direction and the outputs of the Z-axis driving circuit 66 for each of the individual images onto the recording device 70, and also constructs three-dimensional images with reference to the data and outputs and displays the images on the monitor.

The photodiode 17 is connected to the power source through the resistor R1 as shown in FIG. 2 and is always generating light when the power source of the controlling part 3 is ON. When the electric connector 11 is connected to the controlling part 3, the outgoing light of the photodiode 17 is obstructed by the connection part 13 so that the light does not enter the phototransistor 18, which is connected through the resistor R2 to the power source. When no light is detected by the phototransistor 18, no potential difference is generated across resistor R2, and the electric potential of the output part 20 becomes +5V. On the other hand, when the electric connector 11 is disconnected from the controlling part 3, the outgoing light of the photodiode 17 is received by the phototransistor 18 so that a potential difference is generated across resistor R2 and the electric potential of the output part 20 becomes 0 V. The laser driving circuit 64 is controlled by the connection detection circuit 71 of FIG. 8 so that when the output part 20 is +5V, the semiconductor laser 35 of FIG. 5 is driven and when the output part 20 is 0 V, the semiconductor laser 35 stops.

Although in FIG. 2, only three electric cables 15 are shown, the controlling part 3 possess a sufficient number of electric cables which are necessary for the controlling part 3 to receive signals from the photodiode 41 and the phototransistor 18 and to send the controlling signals to control the semiconductor laser 35, electrodes 54a, 54b, 55c, 55d and the Z-axis actuator .23 as shown in FIG. 8.

Although in this embodiment, the half mirror film 40 was provided at the tip of the semiconductor laser 35, this film is not limited to a half mirror film. Alternatively, a dichroic mirror film which changes its reflectance in accordance with wavelength may be provided.

Figure 10:
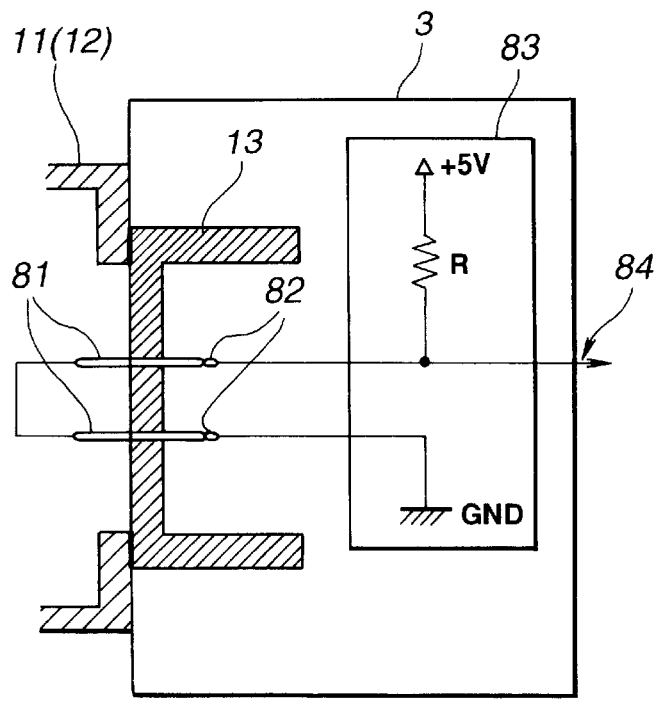

As a modification example of this embodiment, instead of the pins 14 in FIG. 2, shortened pins 81 may be substituted as shown in FIG. 10, pins 82 is provided in the controlling part 3 so as to contact the pins 81 at the time when the connector is connected so that the electric potential of the output part 84 of the signal output circuit 83 becomes 0 V, while upon disconnection the circuit is opened between the pins 82 so that the electric potential of the output part 84 becomes +5V, and the connector connection detection circuit 71 may be controlled to drive the laser when the output part 84 is 0 V and to suspend the laser when it is +5V.

(Advantages)

As described above, in the light scanning probe 1 of this embodiment, since a semiconductor laser 35 is provided at the tip structure part 2 disposed at the distal end of a tube 4 for insertion into a body cavity to irradiate a light onto the subject part to be examined, it is unnecessary to transfer the laser light using an optical fiber, thus making it possible to manufacture the tip structure part 2 and tube 4 with relatively small outside diameters. Moreover, the burden of having to adjust its position upon introduction of the laser light into the optical fiber can be eliminated. In addition, since loss of the laser light during transfer of the light does not occur, the output from the laser light source is used more efficiently and can be minimized.

In addition, since the scan mirror 36 is provided with a gimbal type structure, the focus point of the laser can be scanned in two dimensions with simple construction.

Further, since the half mirror film 40 is provided only at the exit hole of the semiconductor laser 35, this half mirror film 40 functions as a pin hole, making it possible to easily operate as a confocal optical system.

Furthermore, since the photodiode 41 is provided within the tip structure part 2, the entire optical system can be located within the tip structure part 2 for compactness. In addition, since the laser light can be emitted for imaging without being transferred through a fiber, not only does the loss of luminous energy not occur, but also images can be obtained without any noise due to disturbances along the path of the fiber.

Since both the electric connector 11 and the tip structure part 2 have water-tight structures, after use of the present probe, the electric connector 11 can be separated from the controlling part 3 to soak the probe in a washing/antiseptic solution for washing and disinfecting without risk of the solution leaking inside the unit.

When the electric connector 11 is connected to the controlling part, the laser is driven, and when the connection therebetween is disconnected, the power supply to the laser is suspended. With this feature, electric shock can be avoided.

In addition, since the window part 24 and the connection part 21*d* are both integrally provided on the pipe 21, when only the back end part of the Z-axis actuator 23, (to which the optical unit 22 is attached) is adhesively fixed with this connection part 21*d*, the optical unit 22 is properly positioned at the position where it opposes to the window part 24 so that assembly can be easily accomplished.

Second Embodiment

Since the second embodiment is mostly the same as the first embodiment, only the different features are illustrated while the same reference numerals are used for the same structure and will therefore be omitted from the illustrations.
(Construction)

Although the full schematic diagram of this embodiment is the same as FIG. 1, the electric connector 11 is replaced by an electric/optical connector 201 and the controlling part 3 is replaced by a controlling part 150. And, further, a single mode fiber 156 passes through inside the tube 4. The inside of the tip structure part 2 in FIG. 3 is replaced by a tip part 153 in FIG. 11, and in addition to the electric cable 43 in FIG. 5 and the electric cables 15 in FIG. 2, a single-mode fiber 156 is provided.

Figure 11:
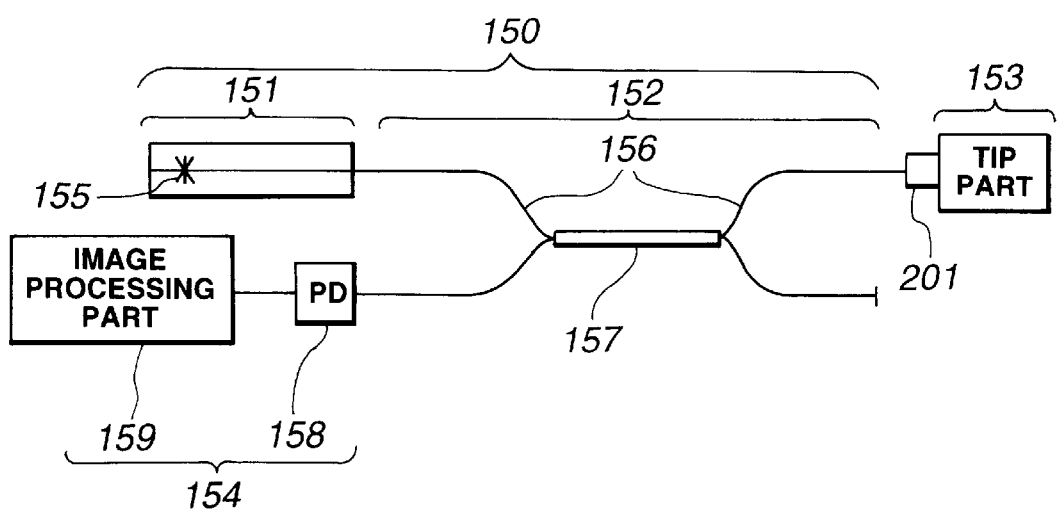
FIG. 11 to FIG. 15 relate to a second embodiment of the present invention.
Figure 12:
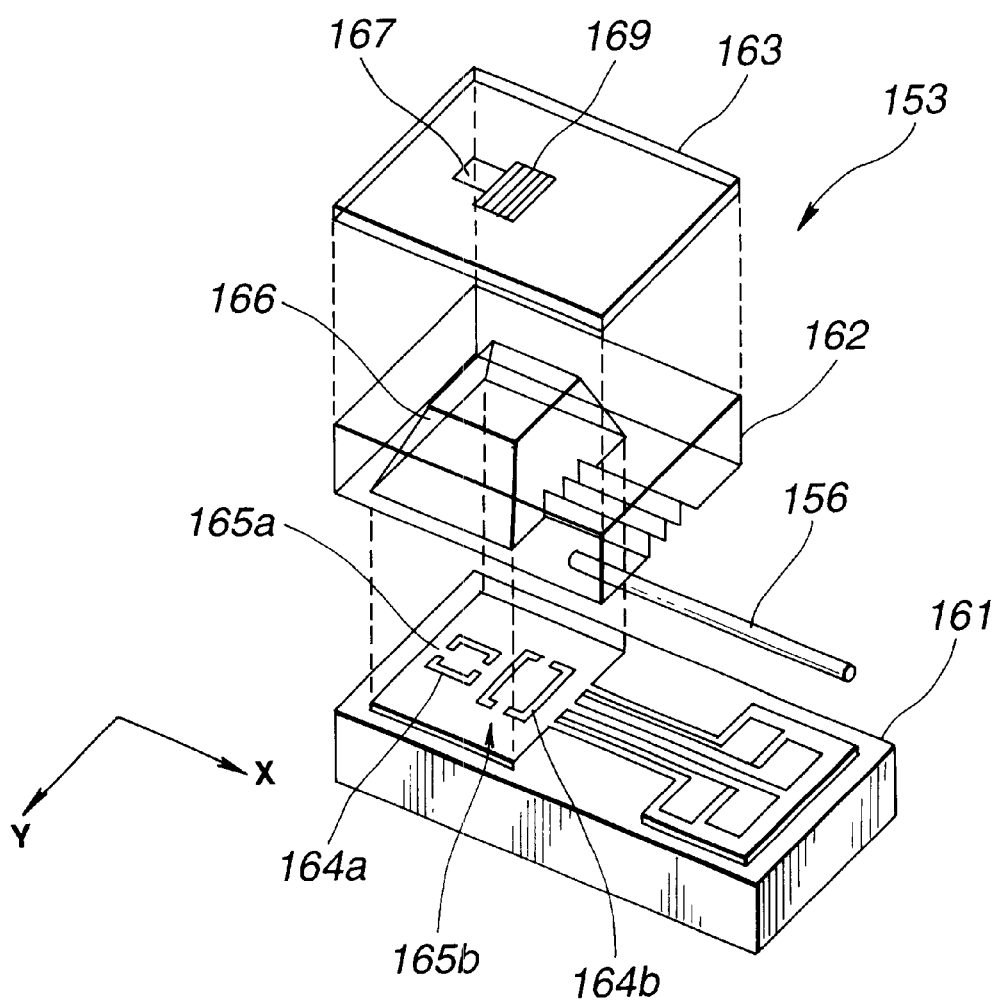

More particularly, as shown in FIG. 11, the controlling part 150 includes a light source part 151, and optical transfer part 152, a tip part 153 and a light detection part 154.

The light source part 151 includes a heliumneon laser which generates a laser light having a wave length of 635 nm, and the light transfer part 152 includes a four-terminal coupler 157 which is connected to single-mode fiber 156 into which the laser light of the laser light source 155 enters and splits the laser light into two beams. One of the other ends of this four-terminal coupler 157 is connected to the tip part 153 through the electric/optical connector 201 while another end is blocked. The light detection part 154 includes a photodetector 158 which is a light detector provided to the four-terminal coupler 157 and an image processing part 159 to which the photo detector 158 is connected.

The tip part 153 includes a substrate 161, a spacer 162 and a top panel 163. The substrate 161 includes two variable mirrors 164*a* and 164*b* having variable positions for scanning the focus of the laser light across a subject matter. These two variable mirrors 164*a* and 164*b* are supported by two hinge parts 165*a* and 165*b*, and are made to be rotatable by static electricity power around the hinge parts 165*a* and 165*b* as the rotation axes. Here, the rotation axes of these two variables mirrors 164*a* and 164*b* are parallel to the X axis and the Y axis which cross at right angles as shown in the figure.

Figure 13:
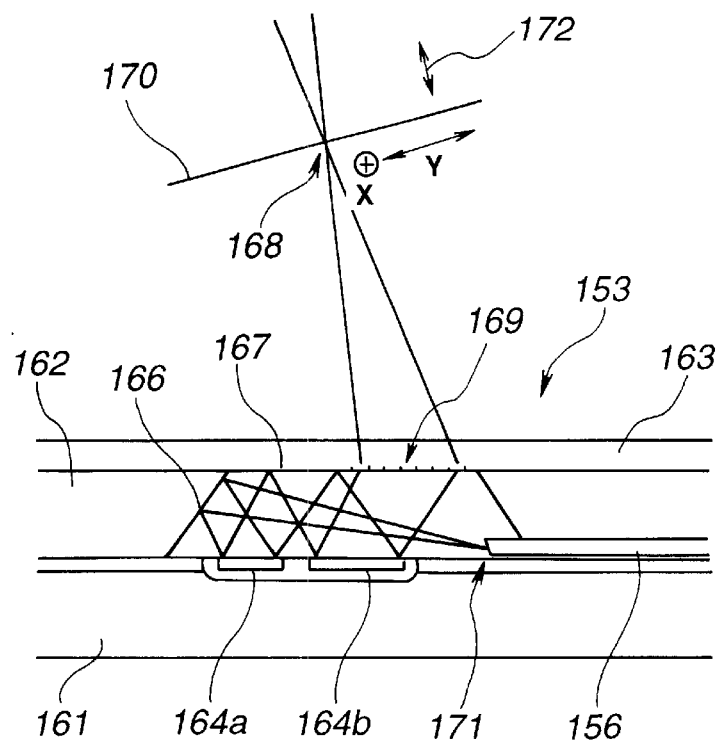

As shown in FIG. 13, a mirror 166 is provided on a surface of the spacer 162, while a mirror 167 and a diffraction grating lens 169 for focusing the laser light at the focus point 168 are provided on the top plate 163.

Figure 14:
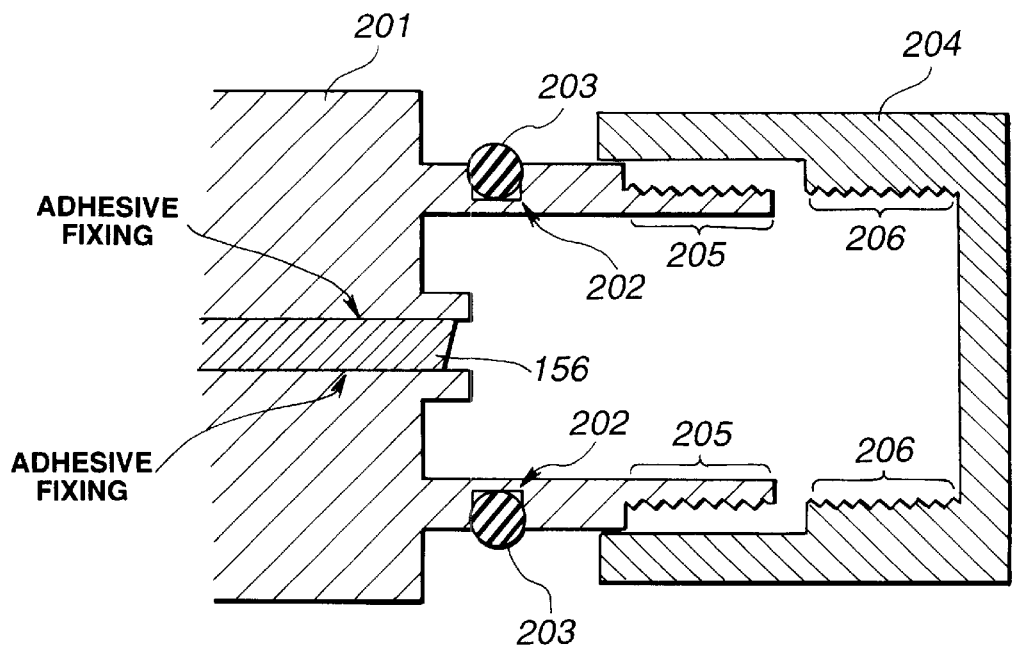

As shown in FIG. 14, a notch part 202 is provided at the base of the electric/optical connector 201, and an O-ring 203 is approximately adhered at the notch part 202. By this O-ring 203, a structure is achieved such that when a water-tight cap 204 made of a metal is secured to the electric/light connector 201, the interior space enclosed by the joined elements is maintained water-tight. At the tip of the light connector 201, a threaded screw part 205 is provided. Also, the bottom of the water-tight cap 204 has a threaded screw part 206 so that when the water-tight cap 204 is screwed onto the electric/optical connector 201 completely, the structure is made to be water-tight.

Moreover, the connected state between the electric/optical connector 210 and the controlling part 150 is detected in the same way as in the first embodiment. Specifically, the outgoing light of the photodiode 17 (not shown) is provided at the side of the controlling part 150 and is projected/blocked to the phototransistor 18 (not shown), which is in line with the photodiode 17 and the surface of the controlling part 150 which contacts the electric/optical connector 201 when connected. The presence or absence of the outgoing light from the photodiode 17 as detected by the phototransistor 18 and is outputted to the connector connection detection circuit 71. Then, the emission of the laser light source 151 is controlled in the same way as in the first embodiment.

Although the electric cables 15 are not shown in FIG. 14, like in the first embodiment, when the electric/optical connector 201 is connected to the controlling part 150, the controlling part 150 is electrically connected to the electric cable 43, similarly shown in FIG. 5, to control the tip part 153 shown in FIG. 11.

Figure 15:
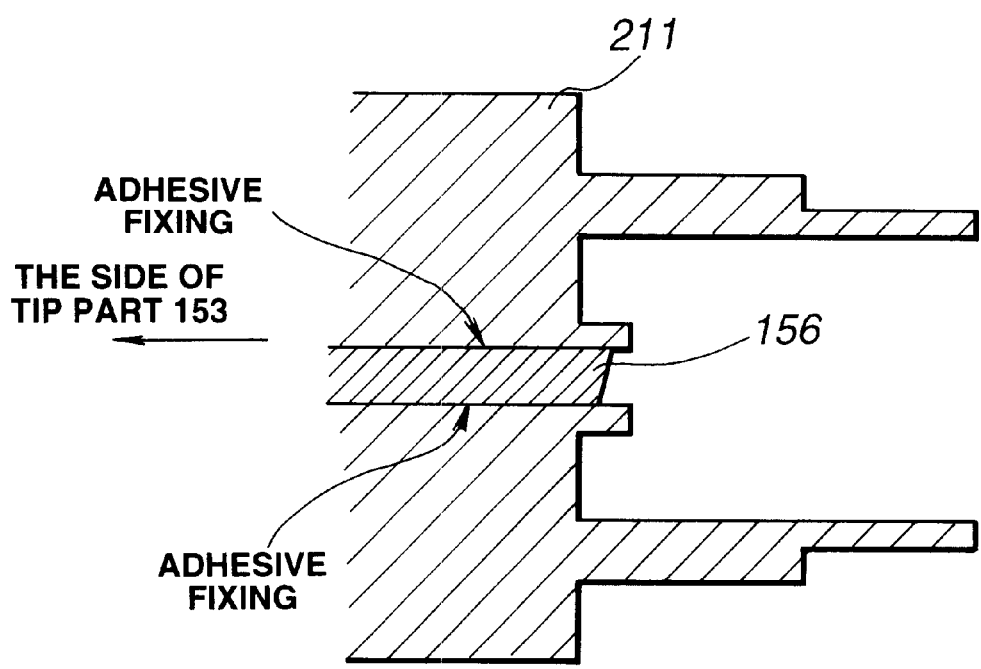
Figure 16:
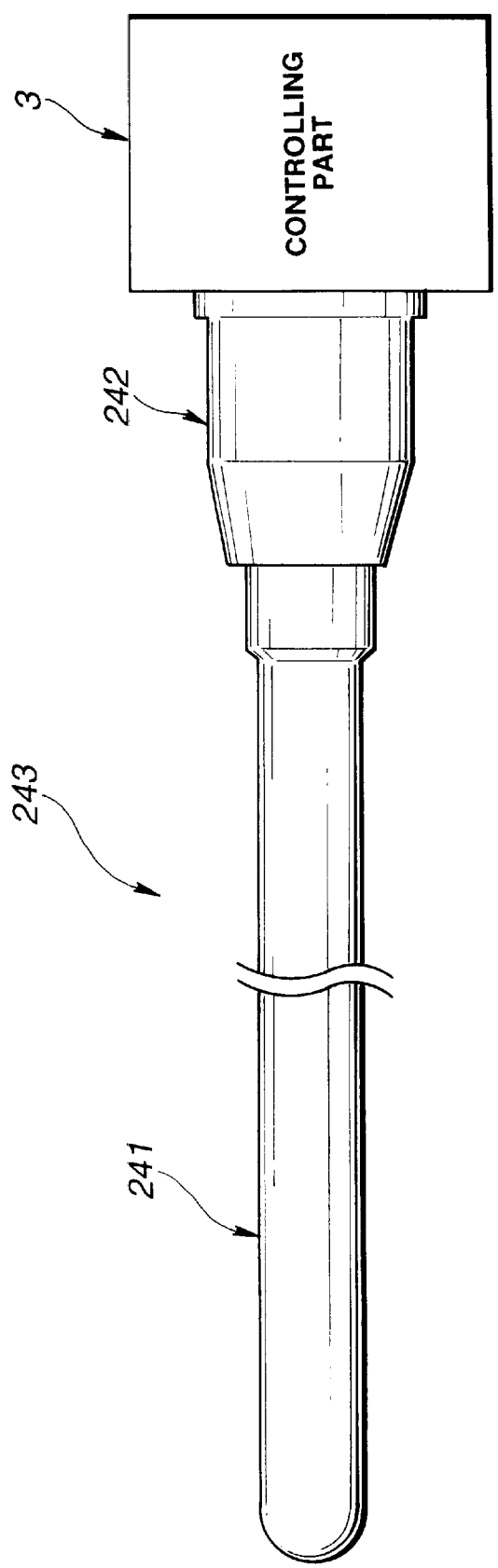
FIG. 16 to FIG. 18 relate to a third embodiment of the present invention.

As a modification example of this embodiment, instead of the electric/optical connector 201 illustrated in FIG. 14, an electric/optical connector 211 as illustrated in FIG. 15 may be used. An electric connection pin or pins, not shown in the figure, as in the first embodiment are also provided in this embodiment.

In each of the embodiments shown in FIGS. 14 and 15, a single-mode fiber 156 may be adhesively fixed in the electric/optical connector 211 to maintain the water-tight structure.

(Operation) At the controlling part 150, the laser light from the laser light source 155 is divided toward two directions at the four-terminal coupler 157, whereupon one of these parts is transmitted to the tip part 153.

This laser light is reflected successively from mirror 166, to movable mirror 164*a*, to mirror 167, and to movable mirror 164*b* in that order, and is then transmitted through diffraction grading lens 169 to focus at focus point 168. In this manner, the focus point 168 is scanned across an approximate plane 170 by the two pivoting mirrors 164*a* and 164*b*, the directions of which can be controlled by shifting and varying the intensity of static electric charge generated thereat.

When a target object is positioned at the location of the focus 168, the laser light is reflected off the target subject and passed through the exact same path as that of the emitted laser light, is focused at the end plane 171 of the single-mode fiber 156 of the four-terminal coupler 157, and then again is transmitted into the single-mode fiber 156. Then, this light is divided by the four-terminal coupler 157 and is detected by the photodetector 158.

When no subject is positioned at the focus 168, no reflected light is returned to be transmitted into the single-mode fiber 156, and therefore no output is made from the photodetector 158. Further, reflected light from a subject having a position deviated from the focus 168 of the laser light has an optical path which is different from that of the incoming light, and therefore does not focus on the end plane 171 of the single-mode fiber 156. Thus, only a small amount of the returning light is transmitted into the single-mode fiber 156, resulting in a low output being produced by the photodetector 158.

As shown in FIG. 14, when the water-tight cap 204 is screwed onto the electric/optical connector 201 completely, the electric/optical connector 201 and the water-tight cap 204 are secured in a water-tight manner by the O-ring 203 so that the inside of the connector is protected by a water-tight structure.

(Advantages)

By scanning the laser light with the mirrors 164a and 164b in the X and Y directions, the changes in intensities of reflection and scattering on the approximate plane 170 where the focus 168 of the laser light scans can be detected on a two-dimension basis, and moreover the image processing part 159 can incorporate these changes into an image of the scanned subject using signals from the photodetector 158. In addition, by changing the distance between the tip part 153 and the subject using a bimorph piezoelectric element (not shown) provided at the tip part 153, said scanning plane is transferred to a direction 172 normal to the X and Y directions as shown in FIG. 13, so as to produce an image of the subject on a three-dimensional basis.

Further, by providing the removable watertight cap 204, the end plane of the electric/optical connector can be protected when it is soaked in a washing/antiseptic solution.

When the electric/optical connector 201 is connected to the controlling part 150, the laser is driven, and when the connection is disconnected, the laser suspends its operations. Due to this feature, leakage of the laser light and electric shock can be avoided.

The Third Embodiment

Since the third embodiment is mostly the same as the first embodiment, only the different features are illustrated, while the same reference numerals are used for the same structures and will therefore be omitted from the illustrations.

(Construction/Operation)

In this embodiment, instead of the tip structure part 2, the tube 4, and the electric connector shown in FIG. 1, a light scanning probe 243 which possesses a clear sheath 241 and a connector 242 is electrically connected to the controlling part 3 in a readily detachable manner.

Figure 17:
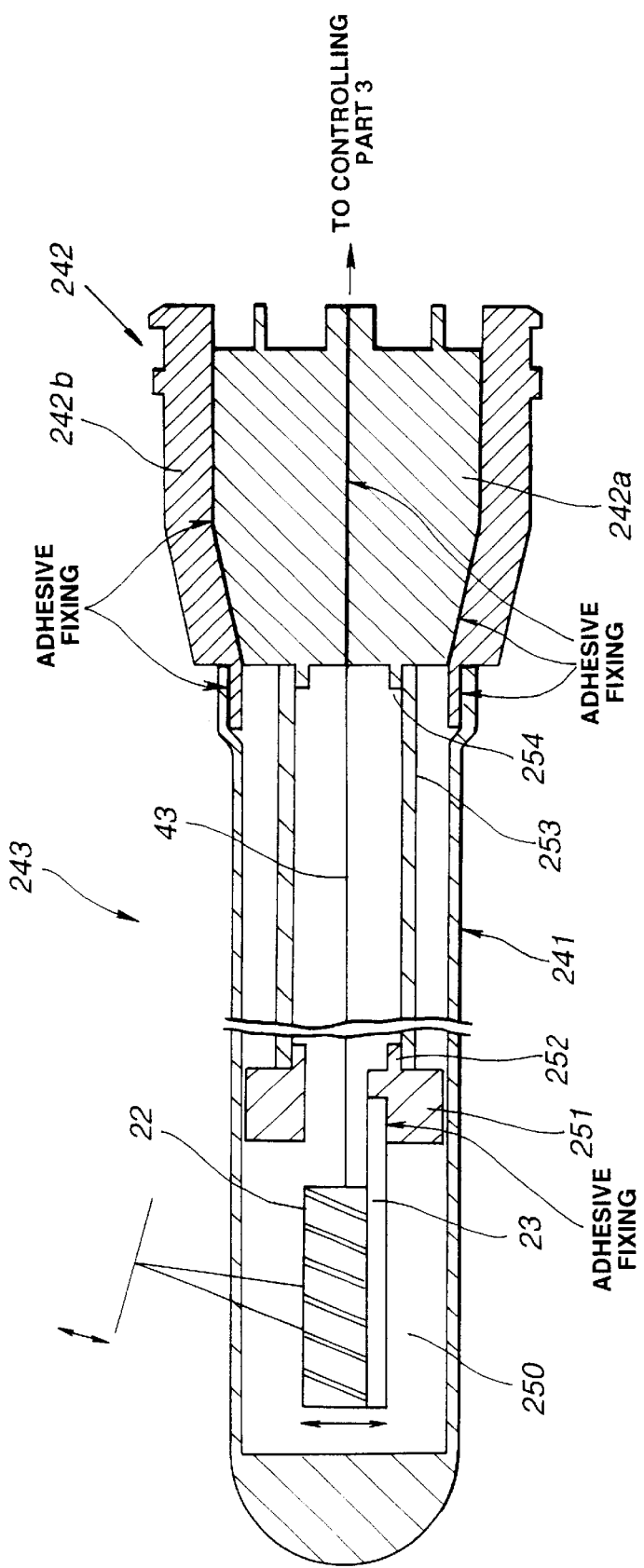

In the light scanning probe 243, as shown in FIG. 17, the proximal end side of the clear sheath 241 and the tip side of the connector 242 are adhesively fixed, and a probe unite 250 which has a structure as described hereinafter is integrated in the clear sheath 241 and the connector 242.

In other words, the back end part of the Z-axis actuator with which the optical unit 22 is fixed is adhesively affixed to a scanner holding member 251, and one end part of a coil pipe 253 is affixed to a coil mounting part 252 of the scanner holding member 251. The other end part of the coil pipe 253 is fixed with a coil pipe connection part 254 of the connector main body 242a of the connector 242. Within the scanner holding member 251 and the coil pipe 253, an electric cable 43.passes through and penetrates through the connector main body 242a, while being adhesively secured in a water-tight manner. With the above-mentioned structure, the probe unit 250 is integrated with the light scanning probe 243 and connector 242.

Around the peripheral part of the connector main body 242a, the armor part 242b of the connector 242 is adhesively secured in a water-tight manner, and the connector 242 is constructed to be removable from and electrically connectable to the controlling part 3.

Here, the sheath 241 may be clear hard resin or a clear soft tube. The light scanning probe 243 is assembled in the following manner. In short, the probe unit 250 is first assembled in advance, and is then inserted into the clear sheath and the connector 242, both of which are adhesively prepared in advance. Finally, the connector 242 is adhesively fixed to the assembly and then the armor part 242b of the connector 242 is adhesively fixed around the peripheral part of the connector main body 242a.

The remaining structures and operations are the same as those of the first embodiment.

(Advantages)

In this embodiment, the optical unit 22 is always assembled so as to be opposed to a clear portion regardless of the direction the probe unit is facing when being affixed during assembly. Thus, assembly becomes easy.

Figure 18:
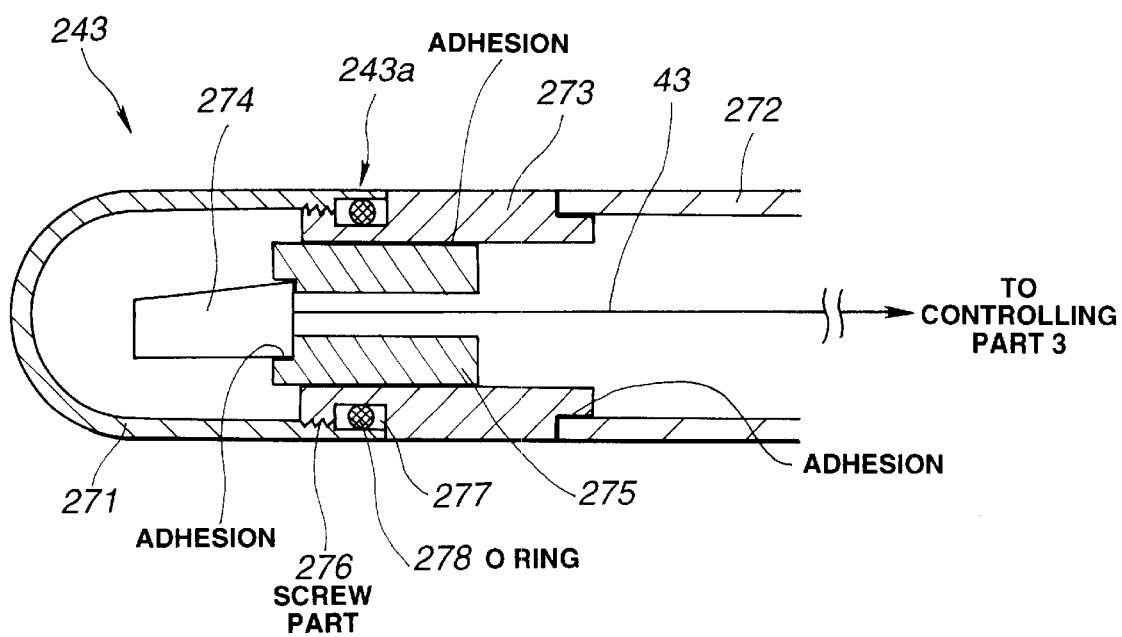

Alternatively, the light scanning probe 243 may be assembled as shown in FIG. 18. That is, instead of the sheath 241, the tip structure part 243a of the light scanning probe 243 may be formed by connecting a hard resin clear cap 271 to the tip of a soft urethane tube 272 via a stainless tip main body 273, and by adhesively fixing the connector 242 with the proximal end of the urethane tube 272, which is not shown in the figure, in a water-tight fashion.

In this case, the scanner part main body 274 which includes of the optical unit 22 and the Z-axis actuator 23 is electrically connected to the electric cable 43, while the electric cable 43 is electrically connected to the controlling part 3 (not shown) through the connector 242 in a readily detachable manner.

The scanner part main body 274 is adhesively fixed with a stainless scanner holding member 275, which is adhesively fixed with the tip main body 273. As shown in FIG. 18, a screw part 276 is threaded on the tip main body 273 so that the resin clear cap 271 can be secured thereto by being screwed onto the tip main body 273. Additionally, a notch 277 is provided around the circumferential surface of the tip main body 273, and a rubber O-ring 278 is placed in the notch 277 so that upon screwing the resin clear cap 271 onto the tip main body, a water-tight structure is achieved. The urethane tube 272 is adhesively affixed to the tip body 273.

The tip structure part 243a is assembled in the following manner. That is, the scanner main body 274 is electrically connected to the electrical cable 43 in advance, and then the electric cable 43 is passed through into the scanner holding member 275 to adhesively fix the scanner part main body 274 to the scanner holding member 275 as shown in FIG. 18. Then, the scanner part main body 274 and the scanner holding member 275 which are adhesively fixed are inserted into the tip main body 273, and the tip main body 273 and the scanner holding member 275 are adhesively fixed as shown in FIG. 18. Then, after passing the electric cable 43 through into the urethane tube 272 as shown in FIG. 18, the urethane tube 272 is adhesively fixed with the tip main body 273. Then, the O-ring 278 is placed into the notch 277 of the tip main body 273, and finally the resin clear cap 271 is screwed onto the screw part 276 of the tip main body 273 to secure it thereto.

By forming the light scanning probe 243 in the way shown in FIG. 18, like the previously described embodiment of FIG. 17, the optical unit 22 is always assembled so as to be opposed to a clear portion regardless of the direction the scanner unit is facing when being affixed during assembly. Thus, the assembly becomes easy. Also, since the scanner part main body 274 is easily exposed merely by removing the resin clear cap 271, repair of the unit is greatly facilitated.

The Fourth Embodiment (Construction)

A light topographic image device 301 shown in FIG. 19 possesses a low coherence light source such as a super high-intensity light emitting diode (referred to as SLD hereinafter) or the like. This low coherence light source 302 emits light which is coherent only within a short distance, for example, a coherent distance range of about 17 μm. That is, when the light is branched into, for example, two beams, and is then reunited within a distance of about 17 μm between the two optical paths from the branching point to the reuniting point, the light is detected as a coherent light. When the distance between the two optical paths is increased, the light becomes non-interactive.

The light of this low coherence light source 302 is emitted into one end of the first single-mode fiber 303 and then transferred to the other end (towards the tip).

This first single-mode fiber 303 is optically bound to the second single-mode fiber 305 by the light coupler part 304 which is positioned along their lengths thereof. Therefore, the light traveling through one of these fibers is branched into two upon reaching the light coupler 304 so that one branch of light is transferred to the other fiber.

Figure 19:
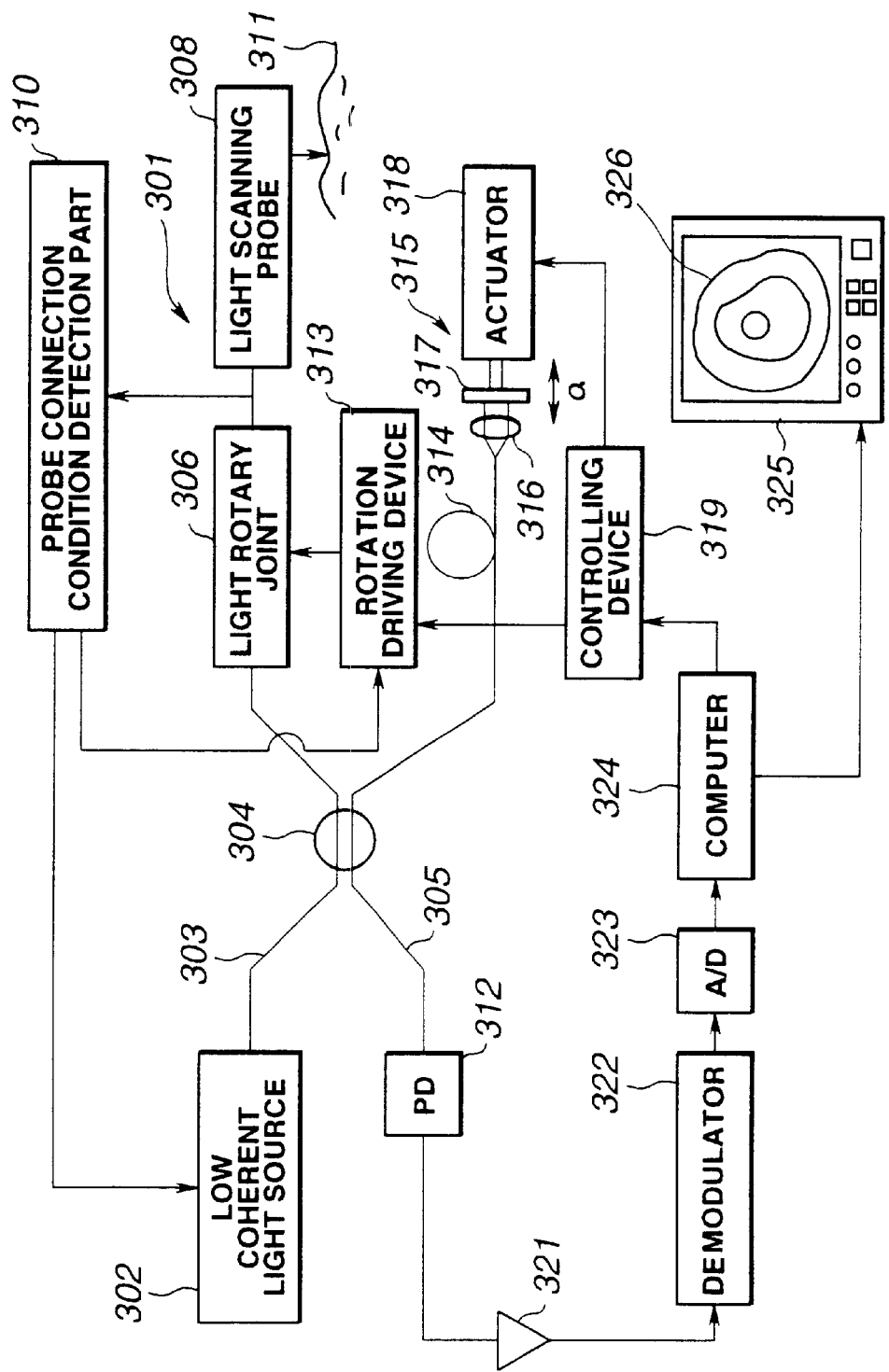
FIG. 19 to FIG. 26 relate to a fourth embodiment of the present invention.
Figure 21:
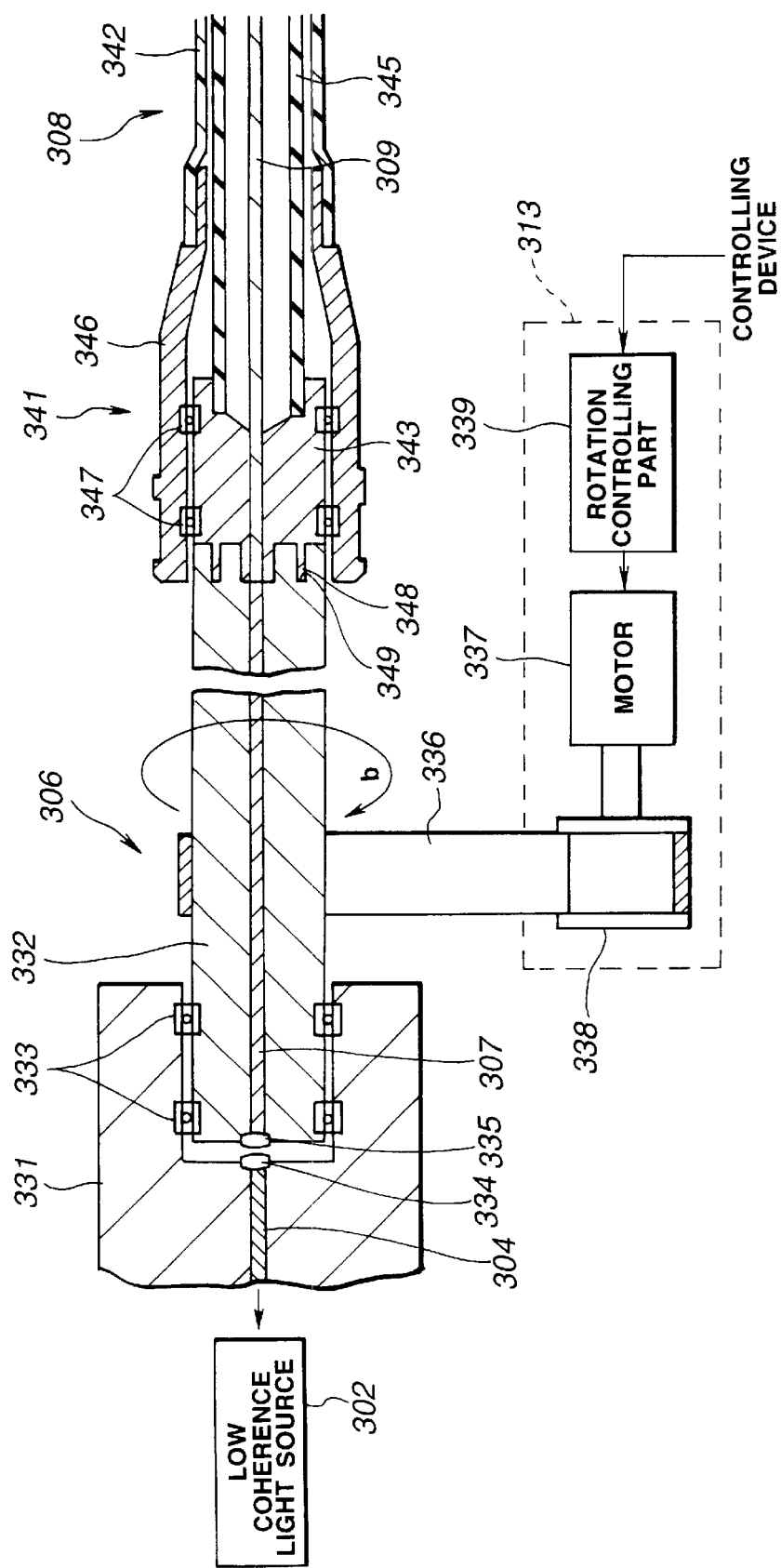

At the tip side of the first single-mode fiber 303 (to the right of coupler 304 as seen in FIG. 19), a light rotary joint 306 which provides a transmittable connection of the light using a non-rotatable part and a rotatable part. The light is introduced into the light scanning probe device (referred to as a light scanning probe hereinafter) 308 through the third single-mode fiber 307 (FIG. 21) within the light rotary joint 306, and then the light of the low coherence light source 302 is transmitted into the fourth rotary-driven single-mode fiber 309 (light-introduction) (FIG. 21).

Then, the transmitted light is emitted in a scanning motion from the tip of the light scanning probe 308 to scan the side of a vital tissue 311. A part of the reflected light which scatters at the surface of or within the side of the vital tissue 311 returns to the side of the first single-mode fiber 303 through the reverse optical path, and a part of it is transferred to the second single-mode fiber 305 by the light coupler part 304, and then is emitted from one end of the second single-mode fiber 305 into a detector for example, the photodiode 312. Here, the rotor of the light rotary joint 306 is driven by a rotation drive device 313.

A light loop part 314 is formed by the second single-mode fiber 305 at a point which is closer to the tip side than the light coupler part 304. Further, an optical path length variable mechanism 315 is provided at the tip side of second single-mode fiber 305.

Specifically, a lens 316 and a mirror 317 are disposed opposite to the tip plane of the second single-mode fiber 305 mirror 317 makes it possible to change the optical path length in the directions shown by an arrow "a" in FIG. 19 via an actuator 318. The light which is reflected at the mirror 317 is mixed with the light which shines though from the first single-mode fiber 303 at the light coupler part 304, and both lights are received at the photodiode 312. The actuator 318 and the rotation drive device 313 are both controlled by the controlling device 319.

Here, the loop part 314 is determined to be almost the same length as the optical path length through the fourth single-mode fiber 309 in the light scanning probe 308. The optical path length of the light exiting from the tip plane of the second single-mode fiber 305 is reflected at the mirror 317 and then returned to the tip plane of the second single-mode fiber 305. This optical path length can be made to be the same as the light path length of the light which is emitted form the tip plane of the fourth single-mode fiber 309 to the vital tissue 311 through a microprism or the like, as will be described hereinafter, and which is then reflected in the inside of the vital tissue 311 and then returned to the tip plane of the fourth single-mode fiber 309.

Then, by changing the position of the mirror 317 in the optical path length variable mechanism 315 to control the standard light so as to change the optical path length, it is possible to cause the standard light to interfere with the reflected light at the position in a depth of the vital tissue 311 which has a value the same as that optical path length, and not with the reflected light at a position in any other depth.

The signal which is photoelectrically converted at the above-mentioned photodiode 312 is amplified with the amplifier 321 and then inputted into a demodulator 322. This demodulator 322 performs extractive demodulation of only the signal part of the interfered light, and the output is inputted into a computer 324 through an A/D converter 323. This computer 324 generates the image data which is used to produce a tomogram, and outputs the image data to a monitor 325 which displays the OCT image 326 on its surface.

This computer 324 is connected to the controlling device 319, and the computer 324 exerts variable control of the optical path length of the standard light through the controlling device 319 and then through the actuator 318, and also controls the scanning direction by rotation through the rotation driving device 313.

The light rotary joint 306 and the light scanning probe 308 are constructed so as to be detachable from each other, and a probe connection detection part 310 which is composed of, for example, a photosensor (not shown) is provided to detect the connection condition between the light rotary joint 306 and the light scanning probe 308. The probe connection detection part 310 is electrically connected to the low coherence light source 302 and the rotation driving device 313 to output the detection signals which show the probe connection conditions to the low coherence light source 302 and the rotation driving device 313.

Figure 20:
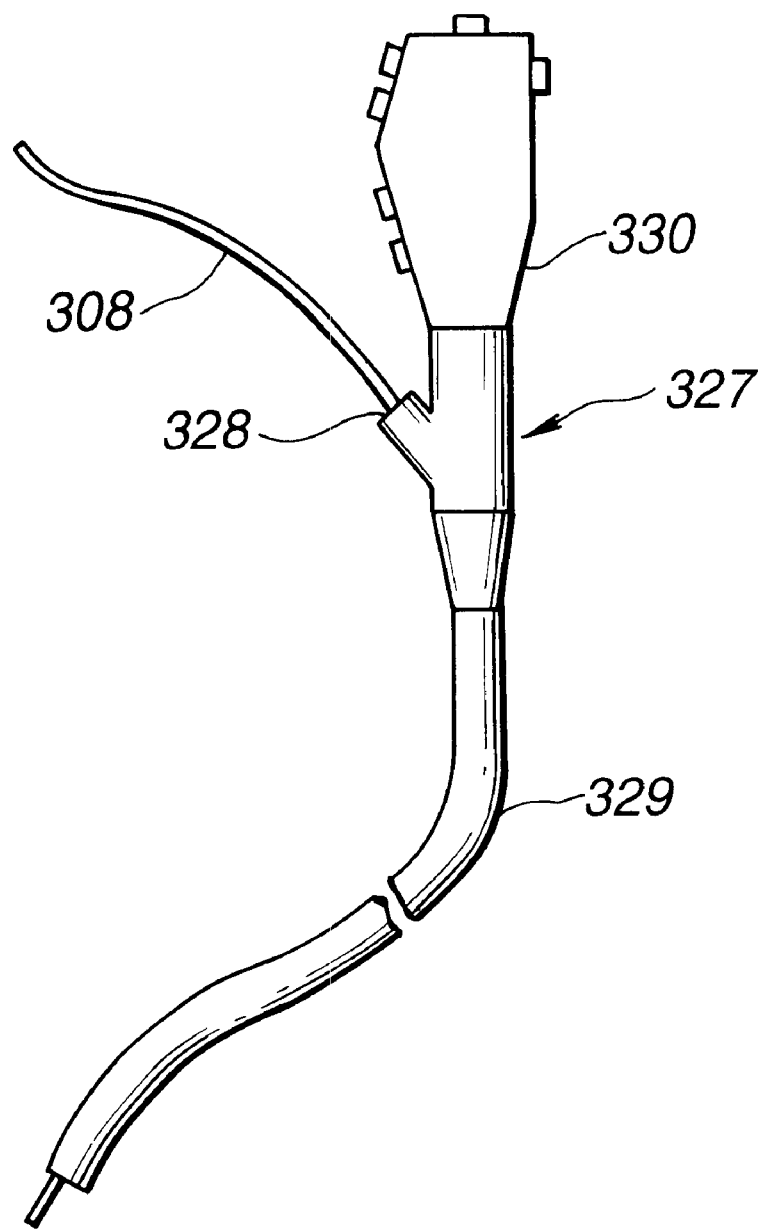

With the light scanning probe 308 of the fourth embodiment, the tip side of the light scanning probe 308 can be inserted into the forceps insertion opening 328 of the endoscope 327, through the forceps insertion channel, and out of the channel tip opening as shown in FIG. 20.

This endoscope 327 includes a slender insertion part 329 for easy insertion into a body cavity, and a wide operation part 330 at the proximal end of the insertion part 329. The forceps insertion opening 328 is provided near the distal end of the operation part 330, and the forceps insertion opening 328 is in communication with the forceps insertion channel inside the insertion part 329.

A light guide, not shown, is inserted in the insertion part 329. The incidence end of the light guide is connected to the light source, and the illuminating light is transmitted to emit from an illumination window provided at the tip part of the insertion part 329, so as to illuminate an affected area or the like. An observation window is provided next to the illumination window, and an objective optical system is installed in the insertion part behind the observation window to enable observation of the illuminated affected area or the like.

More specifically, to enable observation with the observation optical system at the tip part of the endoscope 327, a low coherence light is emitted to illuminate the targeted area, such as an affected area or the like, of the vital tissue 311. Tomographic image data of the inside of the vital tissue 311 is then obtained, and the OCT image 326 is displayed on the display screen of the monitor 325.

The structure of the light scanning probe 308 of this fourth embodiment will be illustrated with reference to FIG. 21 through FIG. 26 hereinafter.

The tip side of the first single-mode fiber 303 is optically bound to the fourth single-mode fiber 309 in the light scanning probe 308 through the third single-mode fiber 307 within the light rotary joint 306 shown in FIG. 21.

A rotor bearing 331 is provided at the tip of the first single-mode fiber 303. A rotor 332 is interfitted into a concave portion of the rotor bearing 331, and the rotor 332 is supported so as to be rotatable (contrary to the non-rotatable rotor bearing 331) by the two rotor bearings 333 disposed between the two.

The first single-mode fiber 303 and the third single-mode fiber 307 are inserted into the rotor bearing 331 and the rotor 332, respectively, with convex lenses 334 and 335 being respectively disposed at the end planes to which the both fibers 303 and 307 are opposed, so that light is effectively transmitted between the nonrotatable fiber 303 and the rotatable fiber 307.

Moreover, the rotor 332 is connected to a pulley 338 of motor 337 in the rotary driving device 313 by, for example, a belt 336. The rotor 332 rotates in response to the rotation of the motor 337 in the direction shown by the arrow "b", which in turn causes the third single-mode fiber 307 to rotate. The motor 337 rotates with a constant speed by means of the motor driving signal from the rotation controlling part 339.

A connector part 341, provided at the proximal end of the light scanning probe 308, is connected to the tip of the rotor 332.

Figure 22:
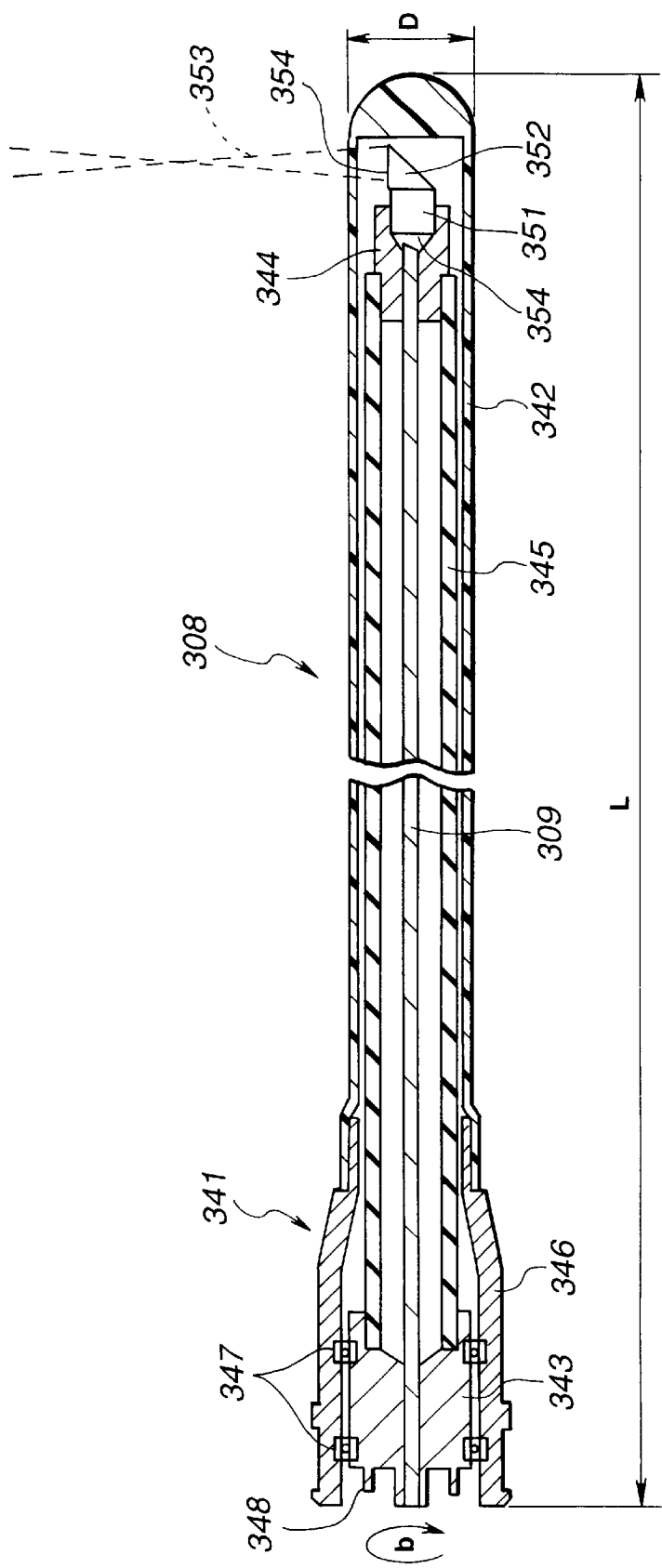

As shown in FIG. 22, in the light scanning probe 308, the fourth single-mode fiber 309 is disposed within the central shaft of slender, cylindrical sheath 342. The back end and the tip of the fourth single-mode fiber 309 are fixed with the connector main body 343 and the tip main body 344, respectively. Additionally, the fourth single-mode fiber 309 is covered with a flexible shaft 345 which serves as a hollow, flexible torque transfer member. The inner diameter of the flexible shaft 345 is slightly larger than the outside diameter of the fourth single-mode fiber 309.

The core diameter of the fourth single-mode fiber 309 is, for example, about 9 μm.

The sheath 342 is formed as a tube of a material which has an excellent near-infrared transparency, such as polymethyl pentene, fluoroplastic, and the like. The sheath 342 is formed so that the tip side is sealed by heat-sealing a member of the same material at the tip of the tube of the material. Also, the sheath 342 is adhesively fixed with the connector part 341. Therefore, the light scanning probe 308 is made to be water-tight except for the back end thereof.

Figure 23:
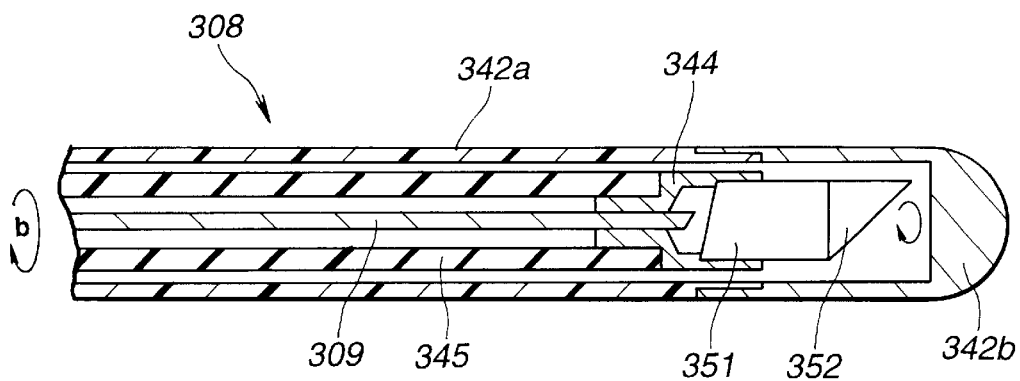

The sheath 342 may alternatively have a structure such as the one shown in FIG. 23. That is, the structure may include a cap 342b which is also made of the above-mentioned material having the excellent near-infrared transparency. The cap 342b may be fitted onto the tip side 342a of the sheath 342a, and the two parts are adhesively fixed together.

Figure 24:
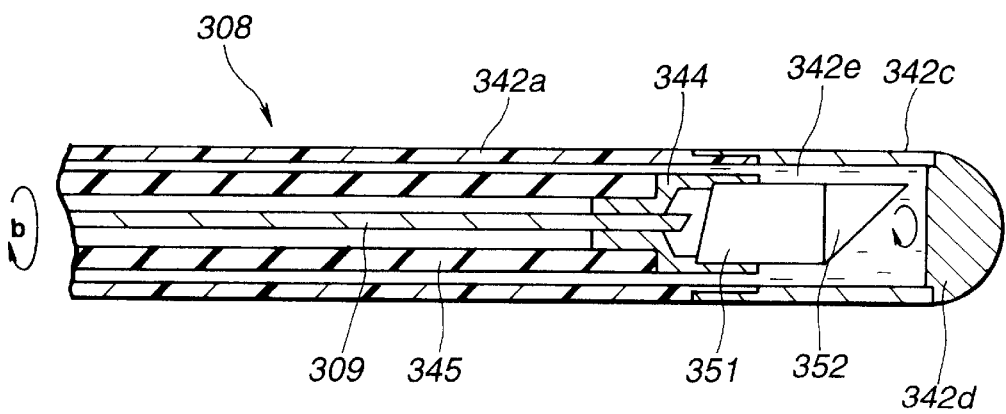

In addition, the sheath 342 may have a structure as shown in FIG. 24. That is, the structure of sheath 342 may include a pipe 342c made of a material such as quartz glass or the like with an excellent near-infrared transparency is fitted onto the tip side 342a of the sheath 342, wherein pipe 342c has openings at both ends, and a cap 342d is fitted onto the tip side of pipe 342c. Furthermore, the contacting surfaces between the tip side 342a of the sheath 342 and the pipe 342c and the contacting surfaces between the pipe 342c and the cap 342d may be adhesively fixed.

In the embodiment of FIG. 24, the inside of the pipe 342c may be filled with a liquid 342e having an appropriate refractivity before the cap 342d is fitted onto the pipe 342c. The refractivity of the liquid 342e is preferably approximately the same as that of the pipe 342c. The reflection of the low coherence light from the inside of the pipe 342c can thus be desirably reduced, since reflection from the inside of the pipe 342c has harmful effects such as causing noise during imaging.

In the flexible shaft 345, a closed winding coil (not shown) is disposed which is coiled double or triple to provide the shaft with its flexibility and so that the shaft can effectively transmit a rotation motion from one end thereof to the other end. Also, the back end and the tip of this flexible shaft 345 are fixedly secured to the connector main body 343 and the tip main body 344, respectively.

The back end of the sheath 342 is secured to a cylindrical connector cover 346 which forms the connector part 341, and the cylindrical connector main body 343 is supported in a rotatable manner there-through by being inserted into bearings 347 provided at two points within connector cover 346. The back end of the fourth single-mode fiber 309 is inserted into a hole provided through the center of the connector main body 343 and is secured by, for example, an adhesive agent or the like.

A convex part 348 is provided at the back end plane of connector main body 343, while a concave part 349 (FIG. 21) which interfits with the convex part 348 is provided at the tip plane of the rotor 332 so that these parts can be interlocked with each other. Thus, when the rotor 332 is rotated while the parts are interlocked, the connector main body also rotates. This torque is communicated to the back end of the flexible shaft 345, and is then transferred to the tip of flexible shaft 345 so as to rotate the tip main body 344 which is disposed at the tip thereof.

Figure 25:
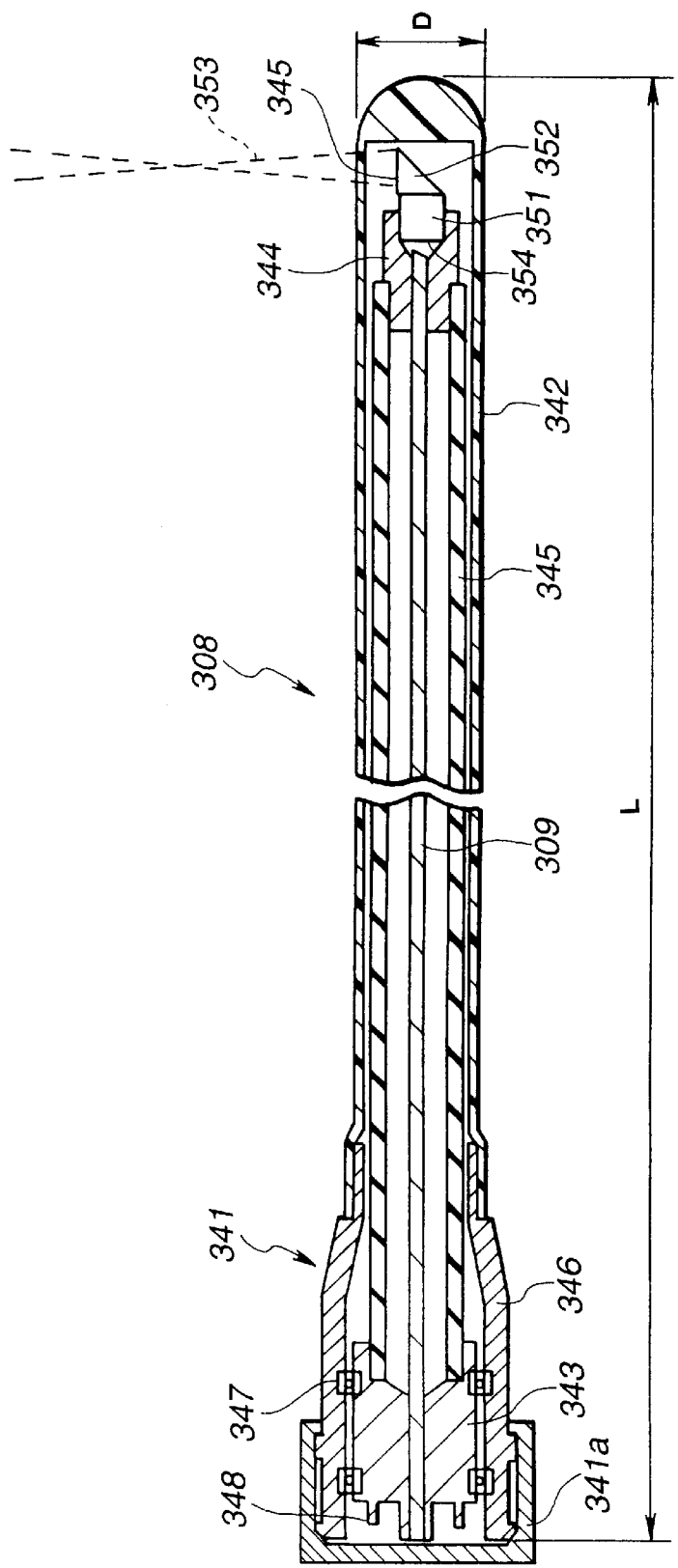

As mentioned above, the light rotary joint 306 and the light scanning probe 308 are formed to be readily detachable from each other. When the light scanning probe 308 is separated from the light rotary joint 306, by fitting a water-tight cap 341a on the connector part 341 of the light scanning probe 308, the light scanning probe 308 can be provided with a water-tight/pressure tight structure, as shown in FIG. 25.

Figure 26:
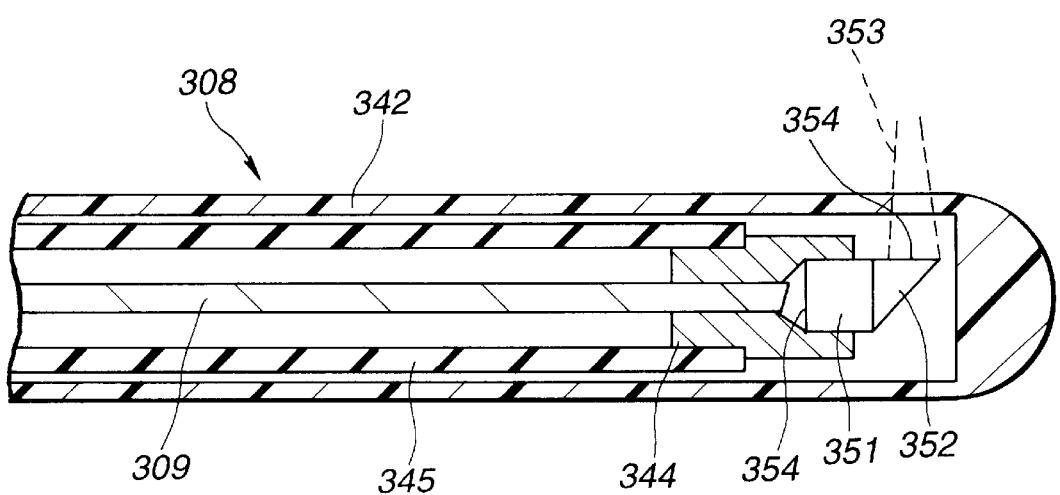

As shown in FIG. 26, the tip of the fourth single-mode fiber 309 is inserted into a hole provided through the center of the tip main body 344 and secured by, for example, an adhesive agent or the like. A self-focusing lens (a GRIN lens) 351, which focuses the outgoing light emitted from the tip of the fourth single-mode fiber 309 at a certain position, is secured near the front end of the fourth single-mode fiber 309 in a widened portion of the hole through tip main body 344. A microprism 352, which alters the optical path by reflection is secured by, for example, an adhesive agent or the like to the tip plane of GRIN lens 351.

Light which is introduced into the fourth single-mode fiber 309 is disposed with a certain clearance at the tip plane thereof before being focused by the GRIN lens 351, and is then perpendicularly reflected in the microprism 352 so that the outgoing light 353 is made to pass through the clear sheath 342 and to focus at a point exterior thereto (as a low coherence light). Around this exterior focal point of the light, a sphere of illumination is created which has a diameter of, for example, from 10 μm to 30 μm.

The tip plane of the fourth single-mode fiber 309 is cut at an angle so as to reduce the readmission of light which is reflected from the back end of the GRIN lens onto the tip plane. In addition, an antireflection film 354 is provided such as by coating an antireflective material onto the rear surface of the GRIN lens and of the microprism 352 to reduce the generation of reflected light.

The tip of the sheath 342 is enclosed in a hemispherical shape. The light scanning probe 308 of this embodiment has an overall length L of about 2000 mm and a sheath diameter D of about 2.4 mm.

(Operation)

By introducing the illumination light from the endoscope light source with the light guide of the endoscope, the surface of the vital tissue 311 (FIG. 19) is illuminated from the illumination window of the tip part of the insertion part 329. The illuminated vital tissue 311 is imaged onto a solid projection element by an optical system located behind the observation window and, after the signal is processed by a video processor, the endoscopic image is displayed on the display monitor.

When a tomogram is displayed by means of a low coherence light, the light scanning probe 308 is inserted into the forceps insertion opening 328 of the endoscope 327 and then is extruded from the tip opening through the inside of the forceps channel as shown in FIG. 20.

Moreover, the connector part 341 at the back end of the light scanning probe 308 is connected to the rotor 332 at the front end of the light rotary joint 306 to form the light tomographic image device 301 shown in FIG. 19.

Then, the low coherence light of the low coherence light source 302 is emitted into the back end of the first single-mode fiber 303 and travels into the back end of the fourth single-mode fiber 309 in the light scanning probe 309 through the third single-mode fiber 307 in the light rotary joint 306.

The low coherence light is thus introduced through this fourth single-mode fiber 309 and emitted from the tip plane onto the opposing GRIN lens 351 as shown in FIG. 22 or FIG. 26. The light is then condensed by the GRIN lens 351 and passed into the microprism 352 which is adhesively fixed at the tip plane of the GRIN lens 351, and then is totally reflected at the slanted face of the microprism 352. The outgoing light 353 is emitted in a direction which differs from its traveling direction by 90°, and illuminates the surface of the vital tissue 311 in the direction at which this outgoing light is emitted.

As shown in FIG. 21, since the rotor 332 forming the light rotary joint 306 is connected to the pulley 338 installed on the center shaft of the motor 337, by rotating the motor 337 at a constant speed, the rotor 332 also rotates at a constant speed in the direction shown by the arrow "b". The connector main body 343 at connection part 341 which is connected to the tip of rotor 332 also rotates with the rotor 332.

Since the back end of the flexible shaft 345, which covers the fourth single-mode fiber 309, is secured with the connector main body 343, flexible shaft 345 also rotates, whereby the torque is transferred through the flexible shaft 345 to its tip. In this case, since the back end of the fourth single-mode fiber 309 is secured in the central hole of the connector main body 343, this fourth single-mode fiber 309 rotates with the flexible shaft 345.

The tip main body 344, which is installed at the tip of the flexible shaft 345 and has the tip of the fourth single-mode fiber 309 secured in its central hole, also rotates. The GRIN lens 351 and the microprism 352, which are fixed with the tip main body 344, also rotate so that the outgoing light 353 shown in FIG. 22 or FIG. 26 scans radially in a direction perpendicular to the axis of the light scanning probe 308.

Then, at a portion (a portion where the reflective index changes) of the vital tissue 311 where the optical characteristics of the internal tissue at the surface or near to the surface changes, the outgoing light is reflected and is also scattered in the tissue. A portion of this light is admitted into the tip plane of the fourth single-mode fiber 309 through the microprism 352 and the GRIN lens 351 in an optical path opposite to that of the emission, and is then transferred to the back end thereof.

The light is admitted into the tip plane of the first single-mode fiber 303 through the third single-mode fiber 307 within the light rotary joint 306, and a portion of the light is transferred to the second single-mode fiber 305 by the light coupler part 304 which is positioned along the path of the first single-mode fiber 303, whereupon this transferred light is mixed with standard light (which is the light reflected from the mirror 317) and then is received at the photodiode 312 and photoelectrically converted into an electric signal.

After this signal is amplified by the amplifier 321, only the coherent light components are extracted and detected. Then, they are converted into digital signals and inputted into the computer 324.

The computer 324 obtains tomographic data at a desired depth and direction of the vital tissue 311 by changing the optical path length with the optical path length variable mechanism 315, while also controlling the rotation driving device 313 through the controlling device 319 to rotate the internal motor 337 at a constant speed. In this manner, one frame of tomographic data is obtained.

The computer 324 can store the tomographic data of a plurality of sequentially obtained frames in its inner image memory, and then read them out according to a specified cycle to display the tomograms or OCT images 326 on the monitor 325 as shown in FIG. 19.

When the light scanning probe 308 is not connected to the light rotary joint 306, a mode signal which indicates "probe disconnect" is outputted from the probe connection detection part 310 to the low coherence light source 302 and to the rotation driving device 313 so that the low coherence light source 302 and the rotation driving device 313 are locked so as to be inoperable. When the light scanning probe 308 is thereafter reconnected to the light rotary joint 306, a mode signal which indicates "probe connect" is outputted and the locks on the low coherence light source 302 and the rotation driving device 313 are released.

On the other hand, if the light scanning probe 308 is initially connected to the light rotary joint 306, and the low coherence light source 302 and the rotation driving device 313 are in their operational state, when the light scanning probe 308 is thereafter detached from the light rotary joint 306, the mode signal designating "probe disconnection" is outputted from the probe connection detection part 310 to the low coherence light source 302 and the rotation driving device 313, so that the operations of the low coherence light source 302 and the rotation driving device 313 are immediately suspended.

Since the light rotary joint 306 and the light scanning probe 308 are formed to be removable, when the light scanning probe 308 is broken during operation or otherwise and therefore becomes unusable, for example, an operator can exchange it for a spare light scanning probe. Moreover, after completion of the examination procedure, by removing the light scanning probe 308 from the light rotary joint 306 and putting the water-tight cap 341a on the connector part 341 of the light scanning probe 308, the light scanning probe 308 can be soaked in a liquid such as a drug solution or the like without damaging the inside functions of the light scanning probe 308.

(Advantages)

In this embodiment, by rotatively driving the fourth single-mode fiber 309 which is centrally disposed within the shaft of the light scanning probe 308, and also by rotatively driving the GRIN lens 351 and the microprism 352 which are provided in the tip of light scanning probe 308, the low coherence light can be scanned steadily in a radial direction perpendicular to the central shaft of the light scanning probe 308. Therefore, the low coherence light can be swept along two dimensions in the circumferential direction so that tomograms at different depths and directions can be readily obtained.

Specifically, tomograms of a circumferential surface can be obtained by scanning in the circumferential direction a wall part of a narrow lumen, for example. This, the observation of surface conditions by the endoscope 327 and diagnosis such as detection of characteristics of the inside lesion area via tomograms can be effectively conducted.

As another example, when an affected area or the like is detected in a vital tissue 311 in a tissue cavity using the endoscope 327 and the inside conditions thereof are desired to be observed more closely, the tip of the light scanning probe 308 is brought closer to the affected area (for example, the tip of the light scanning probe 308 is brought almost parallel to the surface of the affected area) to obtain tomograms by circumferential scanning.

At this point, a narrow portion of the affected area may be displayed on the monitor 325 instead of the broader circumferential tomograms. In this manner, the light scanning device can be used in the inside of a wide lumen, and can also be used in a narrow lumen and when a detailed tomogram is desired to be obtained for only a portion of the wider lumen.

In addition, rotational speeds (i.e., scanning speeds) may be variable in accordance with whether complete circumferential tomograms or partial tomograms of the circumference are to be obtained.

The light scanning device according to this embodiment can be readily used with the existing endoscopes 327 which have a forceps channel to obtain not only tomograms of the surface of the affected area and the like, but also can be used to obtain tomograms of its inside due to the stable light scanning mechanisms described herein. Thus, a light scanning probe 308 which enables more precise diagnosis is provided.

Moreover, because the low coherence light source 302 and the rotation driving device 313 are inoperable due to the locking mechanism of the low coherence light source 302 and the rotation driving device 313 when the light scanning probe 308 is not mounted, operators and patients can be protected from exposures to unnecessary risks.

In addition, if the light scanning probe 308 is broken, the procedure can be resumed merely by exchanging the light scanning probe for a spare without having to exchange the entire device. In particular, it would be necessary to exchange only the relatively inexpensive light scanning probe without exchange the more expensive light rotary joint.

For endoscopes to be used in a variety of testing areas such as the esophagus, stomach, colon, and the like, the length of each endoscope is different than those to be used in other areas. Thus, a light scanning probe having an appropriate length can be selected according to the length of the endoscope to conduct the desired procedure.

Moreover, after completion of a procedure, the light scanning probe can be soaked in a drug solution for a certain time period, the light scanning probe can be disinfected/sterilized without causing damage to its functions so that it is not necessary to provide a new light scanning probe for each patient.

In the present invention, it is clear that a wide variety of different embodiments can be constructed based on the disclosure of the present invention without departing from the spirit and scope thereof. The present invention is therefore limited only by the appended claims and not by the specific embodiments described herein.

What is claimed is:

1. A light scanning device comprising:
    a light scanning probe having an insertion part which can be inserted into a body cavity, said probe also having a light scanner at said distal portion of said insertion part to scan light so as to illuminate a subject area within said body cavity,
    wherein said insertion part and said light scanner form a main body of said probe, and
    wherein at least said light scanner is formed so as to be water-tight;
    a controlling device to which said light scanning probe is readily detachably attachable and which receives detection signals from said scanning probe, and
    a connector which is secured to said main body in a water-tight manner and which is connectable to said controlling device so as to detachably attach said light scanning probe thereto, wherein said light scanner includes an electronic scanning device electrically connected to said controlling device, said electronic scanning device including at least one reflective surface that is pivotable about at least two axes, each of said axis extending in a direction different from the other.

2. A light scanning device according to claim 1, wherein said light scanner includes a silicon micromachined scanning element, and the distal end of the insertion part of said probe main body has an opening,
    said light scanning device further comprising a clear cap which is removably connectable to said insertion part at said opening thereof so as to form a water-tight seal, wherein said micromachined scanning element includes a light emitting portion which is positioned to be opposed to said clear cap.

3. A light scanning device according to claim 1, wherein said light scanning probe includes
    a slender, flexible, and cylindrical sheath which is capable of being inserted into a forceps channel of an endoscope, said sheath having at least a tip composed of a type of material with good light-transparency, said tip being formed with no openings;
    a flexible coil shaft provided within said sheath and which is rotatable around a longitudinal axis thereof;
    a single-mode fiber provided within said flexible coil shaft and having a base end and a tip thereof fixed to a base end and tip of said coil shaft, respectively, wherein light emitted from a low coherence light source is admitted into said base end of said single-mode fiber; and
    a lens positioned at a certain distance from the tip of said fiber to focus light emitted from said fiber onto said light scanner, and
    said controlling device includes a rotation driving device to confer torque to said coil shaft.

4. A light scanning device according to claim 3, further comprising a water-tight cap which is capable of being fitted with the outer surface of said sheath so as to provide a water-tight seal and which is removably connectable to said connector.

5. A light scanning device according to claim 1, wherein said light scanning probe includes
   a sheath including a flexible tube which is capable of being inserted into a forceps channel of an endoscope and which has an opening at each of its proximal end and its distal end;
   a pipe adhesively fixed to the distal end of said sheath and composed of a type of material with good light transparency;
   a cap which seals the distal end of said pipe in a water-tight manner;
   a coil shaft provided within said sheath and which is rotatable around a longitudinal axis thereof;
   a single-mode fiber provided within said flexible coil shaft and having a base end and a tip thereof fixed to a base end and tip of said coil shaft, respectively, wherein light emitted from a low coherence light source is admitted into said base end of said single mode fiber; and
   a lens positioned at a certain distance from the tip of said fiber to focus light emitted from said fiber onto said light scanner, and
   said controlling device includes a rotation driving device to confer torque to said coil shaft.

6. A light scanning device according to claim 5, further comprising a water-tight cap which is capable of being fitted with the outer surface of said sheath so as to provide a water-tight seal and which is removably connectable to said connector.

7. A light scanning device according to claim 1, wherein said light scanning probe has a point source of light which supplies light thereto, and
   said controlling device has a reflected light detector to detect light reflected from the subject area within said body cavity.

8. A light scanning device according to claim 1, wherein said light scanning probe has a reflected light detector to detect light reflected from the subject area within said body cavity, and
   said controlling device has a point source of light which supplies light to said light scanning probe.

9. A light scanning device comprising:
   a light scanning probe having an insertion part which can be inserted into a body cavity, said probe also having a light scanner at a distal portion of said insertion part to scan light so as to illuminate a subject area within said body cavity,
   wherein said insertion part and said light scanner form a main body of said probe, and
   wherein said light scanner is formed so as to be water-tight;
   a controlling device to which said light scanning probe is readily detachably attachable and which receives detection signals from said light scanning probe, and
   a connector which is secured to said main body in a water-tight manner and which is connectable to said controlling device, said connector being formed so as to be water-tight, wherein said light scanner includes an electronic scanning device electrically connected to said controlling device, said electronic scanning device including at least one reflective surface that is pivotable about at least two axes, each of said axes extending in a direction different from the other.

10. A light scanning device according to claim 9, wherein said light scanner includes a silicon micromachined scanning element, and said main body of said probe includes a clear sheath.

11. A light scanning device according to claim 9, wherein said light scanner includes a silicon micromachined scanning element, and the distal end of the insertion part of said probe main body has an opening,
   said light scanning device further comprising a clear cap which is removably connectable to said insertion part at said opening thereof so as to form a water-tight seal, wherein said micromachined scanning element includes a light emitting portion which is positioned to be opposed to said clear cap.

12. A light scanning device according to claim 9, further comprising a water-tight cap on said connector so as to provide a water-tight seal.

13. A light scanning device according to claim 9, wherein said light scanning probe includes
   a slender, flexible, and cylindrical sheath which is capable of being inserted into a forceps channel of an endoscope, said sheath having at least a tip composed of a type of material with good light-transparency, said tip being formed with no openings;
   a flexible coil shaft provided within said sheath and which is rotatable around a longitudinal axis thereof;
   a single-mode fiber provided within said flexible coil shaft and having a base end and a tip thereof fixed to a base end and tip of said coil shaft, respectively, wherein light emitted from a low coherence light source is admitted into said base end of said single-mode fiber; and
   a lens positioned at a certain distance from the tip of said fiber to focus light emitted from said fiber onto said light scanner, and
   said controlling device includes a rotation driving device to confer torque to said coil shaft.

14. A light scanning device according to claim 13, further comprising a water-tight cap which is capable of being fitted with the outer surface of said sheath so as to provide a water-tight seal and which is removably connectable to said connector.

15. A light scanning device according to claim 9, wherein said light scanning probe includes
   a sheath including a flexible tube which is capable of being inserted into a forceps channel of an endoscope and which has an opening at each of its proximal end and its distal end;
   a pipe adhesively fixed to the distal end of said sheath and composed of a type of material with good light transparency;
   a cap which seals the distal end of said pipe in a water-tight manner;
   a coil shaft provided within said sheath and which is rotatable around a longitudinal axis thereof;
   a single-mode fiber provided within said flexible coil shaft and having a base end and a tip thereof fixed to a base end and tip of said coil shaft, respectively, wherein light emitted from a low coherence light source is admitted into said base end of said single mode fiber; and
   a lens positioned at a certain distance from the tip of said fiber to focus light emitted from said fiber onto said light scanner, and
   said controlling device includes a rotation driving device to confer torque to said coil shaft.

16. A light scanning device according to claim 15, further comprising a water-tight cap which is capable of being fitted with the outer surface of said sheath so as to provide a water-tight seal and which is removably connectable to said connector.

17. A light scanning device according to claim 9, wherein
said light scanning probe has a point source of light which supplies light thereto, and
said controlling device has a reflected light detector to detect light reflected from the subject area within said body cavity.

18. A light scanning device according to claim 9, wherein
said light scanning probe has a reflected light detector to detect light reflected from the subject area within said body cavity, and
said controlling device has a point source of light which supplies light to said light scanning probe.

19. A light scanning probe, comprising:
a cylindrical container closed at a first end thereof, said cylindrical container being insertable into a body cavity;
a portion of said first end being transparent;
an electronic light scanning member in an interior of said first end;
said electronic light scanning member including a substrate, a light source and at least one reflective surface disposed over said substrate, wherein at least a portion of said at least one reflective surface can be given an electrical potential with respect to said substrate, said electrical potential being effective to provide an electrostatic force to move said at least one reflective surface;
a connector attached at a second end of said container to form a fluid impermeable seal between said connector and said second end; and
a control device which can communicate with said light scanning member; wherein
said connector is attachable to said control device.

20. A light scanning probe according to claim 19, wherein said container is entirely transparent.

21. A light scanning probe according to claim 19, wherein:
said connector includes a plug attachable to said control device; and
said plug is fluid impermeable.

22. A light scanning probe according to claim 19, wherein:
said control device includes a switch accessible to said connector;
said switch and said connector can cooperate to control said light source; and
said switch prevents activation of said light source when not engaged with said connector.

23. A light scanning probe, comprising:
a cylindrical container closed at a first end thereof, said cylindrical container being insertable into a body cavity;
a portion of said first end being transparent;
an electronic light scanning member in an interior of said first end;
said electronic light scanning member including a substrate, a light source and at least one reflective surface, wherein at least a portion of said at least one reflective surface can be given an electrical potential with respect to said substrate, said electrical potential being effective to provide an electrostatic force to move said at least one reflective surface;
a connector attached at a second end of said container to form a fluid impermeable seal between said connector and said second end; and
a control device which can communicate with said light scanning member; wherein
said connector is attachable to said control device and said light source is a semiconductor laser.

24. A light scanning probe according to claim 23, wherein said light scanning member further includes a diffraction grating that can focus light passing therethrough.

25. A light scanner in a fluid impermeable endoscope, comprising:
a light source;
at least one reflective surface on a movable member that can receive light from said light source;
a diffraction grating effective to receive light directed from said at least one reflective surface, said diffraction grating focusing light passing therethrough;
a substrate adjacent said at least one movable member;
a portion of said at least one movable member being effective to receive an electric charge;
an electrical potential between said at least one moveable member and said substrate when said portion receives an electric charge; and
said electrical potential can urge said at least one movable reflective surface with respect to said substrate.

26. A light scanning device comprising:
a light scanning probe including a main body, said main body having an insertion part being insertable into a body cavity and a light scanner at a distal end of said insertion part to scan light to illuminate a subject area within a body cavity, said light scanner including a micromachined scanning element that comprises silicon;
a hollow pipe, said micromachined scanning element being disposed inside said hollow pipe;
a front cover watertightly sealing a distal end of said pipe;
a rear cover watertightly sealing a proximal end of said pipe, and watertightly secured to said insertion part so as to enclose said light scanner within said pipe;
a clear window watertightly disposed on said distal end of said pipe to accommodate a transmission of light to and from said micromachined scanning element;
a controlling device to which said light scanning probe is readily detachably attachable and which receives detection signals or light from said scanning probe; and
a connector which is watertightly secured to said main body and which is connectable to said controlling device so as to detachably attach said light scanning probe thereto.

27. A light scanning device according to claim 26, wherein said front cover, said rear cover, and said window are sealed with said pipe by an adhesive so as to form said water-tight structure.

28. A light scanning device according to claim 26, wherein when said pipe fixed to said micromachined scanning element, and wherein said micromachined scanning element has a light emitting portion which is positioned to be opposed to said window.

29. A light scanning device according to claim 26, wherein said pipe and said window are integrally formed as a hollow clear pipe.

30. A light scanning device according to claim 1, wherein said scanner includes a silicon micromachined scanning element, and said main body of said probe includes a clear sheath.

31. A light scanning device according to claim 26, wherein said light scanning probe includes
  a point source of light which supplies light to said micromachined scanning element;
  a reflected light detector which detects light reflected from said subject area and which transforms the detected light into an electrical signal; and
  an optical system which focuses said light from said point source of light and which focuses the reflected light from said subject area at said reflected light detector, and
said controlling device includes
  a signal processor to process the electrical detection signal from said subject area through said reflected light detector;
  a point source of light driver to electrically drive said point source of light; and
  a light scan driver to electrically drive said micromachined scanning element,
  wherein when said light scanning probe is electrically connected to said controlling device by said connector,
    said micromachined scanning element and said light scan driver are electrically connected,
    said point source of light and said point source of light driver are electrically connected, and
    said reflected light detector and said signal processor are electrically connected.

32. A light scanning device according to claim 31, wherein
said light scanner includes
  a micromachined scanning mirror that includes a silicon member;
  a silicon nitride hinge which supports and rotates said micromachined scanning mirror;
  a reflecting surface which is conducted by the silicon member in order to receive the light from said light source; and
  a mirror driver to electrostatically move said micromachined scanning mirror in order to scan the light toward a first direction and a second direction which is orthogonal to said first direction.

33. A light scanning device according to claim 26, wherein
said light scanning probe includes
  a single-mode fiber to introduce light to illuminate said subject area within said body cavity, and which also receives light reflected from said subject area; and
  an optical system which focuses light onto said subject area while focusing said reflected light from said subject area onto said single-mode fiber, and
said controlling device includes
  a point source of light;
  a light-introducer which introduces light emitted from said point source of light to said single-mode fiber, while receiving and introducing said reflected light from said subject area through said single-mode fiber;
  a light-separator which separates said reflected light from said light-introducer and said light from said point source of light;
  a reflected light detector which detects said reflected light separated out by said light separator; and
  a light scan driver which drives said light scanner,
  wherein when said light scanning probe is connected to said controlling device by said connector, said single-mode fiber and said light-introducer are optically connected, while said reflected light is separated from said light from said point source of light by said light-separator, and said light scanner and said light scan driver are electrically connected.

34. A light scanning device according to claim 33, wherein
said light scanner includes
  a micromachined scanning mirror including a silicon member;
  a silicon nitride hinge which supports and rotates said micromachined scanning mirror
  a reflecting surface which is conducted by the silicon member in order to receive the light from said light source; and
  a mirror driver to electrostatically move said micromachined scanning mirror in order to scan the light toward a first direction and a second direction which is orthogonal to said first direction.

35. A light scanning device according to claim 24, wherein
said light scanning probe has a point source of light which supplies light thereto, and
said controlling device has a reflected light detector to detect light reflected from the subject area within said body cavity.

36. A light scanning device according to claim 24, wherein
said light scanning probe has a reflected light detector to detect light reflected from the subject area within said body cavity, and
said controlling device has a point source of light which supplies light to said light scanning probe.

37. A light scanning device comprising:
a light scanning probe including a main body, said main body having an insertion part being insertable into a body cavity and a light scanner at a distal end of said insertion part to scan light to illuminate a subject area within a body cavity, said light scanner including a micromachined scanning element that comprises silicon;
a hollow pipe, said micromachined scanning element being disposed inside said hollow pipe;
a front cover watertightly sealing a distal end of said pipe;
a rear cover watertightly sealing a proximal end of said pipe, and watertightly secured to said insertion part so as to enclose said light scanner;
a clear window watertightly disposed on said distal end of said pipe to accommodate a transmission of light to and from said micromachined scanning element;
a controlling device to which said light scanning probe is readily detachably attachable and which receives detection signals or light from said light scanning probe, and
a watertight connector which is watertightly secured to said main body and which is connectable to said controlling device.

38. A light scanning device according to claim 37, wherein said front cover said rear cover, and said window are sealed with said pipe by an adhesive so as to form said water-tight structure.

39. A light scanning device according to claim 37, wherein when said pipe is fixed to said micromachined scanning element, and wherein said micromachined scanning element has a light emitting portion which is positioned to be opposed to said window.

40. A light scanning device according to claim 37, wherein said pipe and said window are integrally formed as a hollow clear pipe.

41. A light scanning device according to claim 37, wherein
said light scanning probe includes
a point source of light which supplies light to said micromachined scanning element;
a reflected light detector which detects light reflected from said subject area and which transforms the detected light into an electrical signal; and
an optical system which focuses said light from said point source of light and which focuses the reflected light from said subject area at said reflected light detector, and
said controlling device includes
a signal processor to process the electrical detection signal from said subject area through said reflected light detector;
a point source of light driver to electrically drive said point source of light; and
a light scan driver to electrically drive said micromachined scanning element,
wherein when said light scanning probe is electrically connected to said controlling device by said connector, said micromachined scanning element and said light scan driver are electrically connected, said point source of light and said point source of light driver are electrically connected, and said reflected light detector and said signal processor are electrically connected.

42. A light scanning device according to claim 41, wherein
said light scanner includes
a micromachined scanning mirror including a silicon member;
a silicon nitride hinge which supports and rotates said micromachined scanning mirror;
a reflecting surface which is conducted by the silicon member in order to receive the light from said light source; and
a mirror driver to electrostatically move said micromachined scanning mirror in order to scan the light toward a first direction and a second direction which is orthogonal to said first direction.

43. A light scanning device according to claim 37, wherein
said light scanning probe includes
a single-mode fiber to introduce light to illuminate said subject area within said body cavity, and which also receives light reflected from said subject area; and
an optical system which focuses light onto said subject area while focusing said reflected light from said subject area onto said single-mode fiber, and
said controlling device includes
a point source of light;
a light-introducer which introduces light emitted from said point source of light to said single-mode fiber, while receiving and introducing said reflected light from said subject area through said single-mode fiber;
a light-separator which separates said reflected light from said light-introducer and said light from said point source of light;
a reflected light detector which detects said reflected light separated out by said light-separator; and
a light scan driver which drives said light scanner,
wherein when said light scanning probe is connected to said controlling device by said connector, said single-mode fiber and said light-introducer are optically connected, while said reflected light is separated from said light from said point source of light by said light-separator, and said light scanner and said light scan driver are electrically connected.

44. A light scanning device according to claim 43, wherein
said light scanner includes
a micromachined scanning mirror including a silicon member;
a silicon nitride hinge which supports and rotates said micromachined scanning mirror;
a reflecting surface which is conducted by the silicon member in order to receive the light from said light source; and
a mirror driver to electrostatically move said micromachined scanning mirror in order to scan the light toward a first direction and a second direction which is orthogonal to said first direction.

45. A light scanning device according to claim 35, wherein
said light scanning probe has a point source of light which supplies light thereto, and
said controlling device has a reflected light detector to detect light reflected from the subject area within said body cavity.

46. A light scanning device according to claim 37, wherein
said light scanning probe has a reflected light detector to detect light reflected from the subject area within said body cavity, and
said controlling device has a point source of light which supplies light to said light scanning probe.

47. A light scanning probe, comprising:
a cylindrical container closed at a first end;
a portion of said first end being transparent;
a light scanning member in an interior of said first end;
said light scanning member including a light source, a substrate and at least one movable reflective surface, a portion of which can be given an electric potential with respect to said substrate, said electrical potential being effective to provide an electrostatic force to move said at least one reflective surface;
a connector attached at a second end of said container to form a fluid impermeable seal between said connector and said second end; and
a control device which can communicate with said light scanning member to control a motion of said reflective surface; wherein
said connector is attachable to said control device.

48. A light scanning probe according to claim 47, wherein said control device controls said electrical potential.

* * * * *